(12) United States Patent
Dribinski et al.

(10) Patent No.: US 9,413,134 B2
(45) Date of Patent: Aug. 9, 2016

(54) MULTI-STAGE RAMP-UP ANNEALING FOR FREQUENCY-CONVERSION CRYSTALS

(71) Applicant: KLA-Tencor Corporation, Milpitas, CA (US)

(72) Inventors: Vladimir Dribinski, Livermore, CA (US); Yung-Ho Alex Chuang, Cupertino, CA (US); J. Joseph Armstrong, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/753,275

(22) Filed: Jun. 29, 2015

(65) Prior Publication Data

US 2015/0299893 A1    Oct. 22, 2015

Related U.S. Application Data

(62) Division of application No. 14/507,758, filed on Oct. 6, 2014, now Pat. No. 9,097,683, which is a division of application No. 13/412,564, filed on Mar. 5, 2012, now Pat. No. 8,873,596.

(60) Provisional application No. 61/510,633, filed on Jul. 22, 2011.

(51) Int. Cl.
*H01S 3/10* (2006.01)
*H01S 5/00* (2006.01)
(Continued)

(52) U.S. Cl.
CPC .............. *H01S 5/0092* (2013.01); *C03B 33/02* (2013.01); *C30B 1/02* (2013.01); *C30B 29/10* (2013.01);
(Continued)

(58) Field of Classification Search
CPC .......... H01S 3/11; H01S 3/10046; H01S 3/10; H01S 3/10038; H01S 3/0092
USPC ..................... 372/22, 21, 30, 29.02
See application file for complete search history.

(56) References Cited

U.S. PATENT DOCUMENTS 4,178,561 A    12/1979    Hon et al.
4,467,189 A    8/1984    Tsuchiya
(Continued)

FOREIGN PATENT DOCUMENTS

CN    101702490 A    5/2010
DE    102007004235 B3    1/2008
(Continued)

OTHER PUBLICATIONS

KLA-Tencor Corporation; PCT International Search Report dated Dec. 29, 2015 for Application No. PCT/US2015/051538, 3 pages.
(Continued)

*Primary Examiner* — Kinam Park
(74) *Attorney, Agent, or Firm* — Bever, Hoffman & Harms, LLP

(57) ABSTRACT

A frequency-conversion crystal annealing process includes a first ramp-up period (e.g., increasing the crystal's temperature to a first set point in the range of 100° C. to 150° C. over about 2 hours), a first fixed temperature period (e.g., maintaining at the first set point for 10 to 20 hours), a second ramp-up period (e.g., increasing from the first set point to a second set point above 150° C. over about 1 hour or more), a second fixed period (e.g., maintaining at the second set point for 48 to 300 hours), and then a temperature ramp-down period (e.g., decreasing from the second set point to room temperature over about 3 hours). Transitions from the first and second fixed temperature periods are optionally determined by —OH bonds absorption levels that are measured using Fourier transform infrared spectroscopy, e.g., by monitoring the absorption of —OH bonds (including $H_2O$) near 3580 $cm^{-1}$ in the infra-red spectrum.

20 Claims, 10 Drawing Sheets

(51) Int. Cl.
*H01S 3/11* (2006.01)
*G02F 1/37* (2006.01)
*H01S 3/00* (2006.01)
*C30B 29/10* (2006.01)
*C30B 33/02* (2006.01)
*G01N 21/88* (2006.01)
*G01N 21/94* (2006.01)
*G01N 21/95* (2006.01)
*C03B 33/02* (2006.01)
*C30B 1/02* (2006.01)
*C30B 29/14* (2006.01)
*C30B 29/22* (2006.01)
*C30B 29/30* (2006.01)
*G02F 1/35* (2006.01)
*G02F 1/355* (2006.01)

(52) U.S. Cl.
CPC ............ *C30B 29/14* (2013.01); *C30B 29/22* (2013.01); *C30B 29/30* (2013.01); *C30B 33/02* (2013.01); *G01N 21/88* (2013.01); *G01N 21/8806* (2013.01); *G01N 21/94* (2013.01); *G01N 21/9501* (2013.01); *G02F 1/3551* (2013.01); *G02F 1/37* (2013.01); *H01S 3/0092* (2013.01); *H01S 3/10* (2013.01); *H01S 3/10038* (2013.01); *H01S 3/10046* (2013.01); *H01S 3/11* (2013.01); *G01N 2201/068* (2013.01); *G01N 2201/0637* (2013.01); *G01N 2201/06113* (2013.01); *G02F 1/353* (2013.01); *G02F 1/3553* (2013.01); *G02F 2001/354* (2013.01); *G02F 2001/3505* (2013.01); *G02F 2001/3507* (2013.01); *G02F 2202/20* (2013.01)

(56) References Cited

U.S. PATENT DOCUMENTS

| | | | |
|---|---|---|---|
| 5,108,176 | A | 4/1992 | Malin et al. |
| 5,120,949 | A | 6/1992 | Tomasetti |
| 5,144,630 | A | 9/1992 | Lin |
| 5,189,481 | A | 2/1993 | Jann et al. |
| 5,293,389 | A | 3/1994 | Yano et al. |
| 5,377,001 | A | 12/1994 | Malin et al. |
| 5,377,002 | A | 12/1994 | Malin et al. |
| 5,563,702 | A | 10/1996 | Emery et al. |
| 5,572,598 | A | 11/1996 | Wihl et al. |
| 5,712,701 | A | 1/1998 | Clementi et al. |
| 5,742,626 | A | 4/1998 | Mead et al. |
| 5,760,899 | A | 6/1998 | Eismann |
| 5,825,562 | A | 10/1998 | Lai et al. |
| 5,998,313 | A | 12/1999 | Sasaki et al. |
| 5,999,310 | A | 12/1999 | Shafer et al. |
| 6,002,695 | A | 12/1999 | Alfrey et al. |
| 6,002,697 | A | 12/1999 | Govorkov et al. |
| 6,118,525 | A | 9/2000 | Fossey et al. |
| 6,201,601 | B1 | 3/2001 | Vaez-Iravani et al. |
| 6,212,310 | B1 | 4/2001 | Waarts et al. |
| 6,249,371 | B1 | 6/2001 | Masuda et al. |
| 6,271,916 | B1 | 8/2001 | Marxer et al. |
| 6,373,869 | B1 | 4/2002 | Jacob |
| 6,498,801 | B1 | 12/2002 | Dudelzak et al. |
| 6,590,698 | B1 | 7/2003 | Ohtsuki et al. |
| 6,608,676 | B1 | 8/2003 | Zhao et al. |
| 6,816,520 | B1 | 11/2004 | Tulloch et al. |
| 6,859,335 | B1 | 2/2005 | Lai et al. |
| 6,888,855 | B1* | 5/2005 | Kopf .................. G02B 26/0816 372/21 |
| 7,088,443 | B2 | 8/2006 | Vaez-Iravani et al. |
| 7,098,992 | B2 | 8/2006 | Ohtsuki et al. |
| 7,136,402 | B1 | 11/2006 | Ohtsuki |
| 7,313,155 | B1* | 12/2007 | Mu ....................... A61B 18/20 372/10 |
| 7,339,961 | B2 | 3/2008 | Tokuhisa et al. |
| 7,345,825 | B2 | 3/2008 | Chuang et al. |
| 7,352,457 | B2 | 4/2008 | Kvamme et al. |
| 7,463,657 | B2 | 12/2008 | Spinelli et al. |
| 7,471,705 | B2 | 12/2008 | Gerstenberger et al. |
| 7,492,451 | B2 | 2/2009 | Vaez-Iravani et al. |
| 7,525,649 | B1 | 4/2009 | Leong et al. |
| 7,528,943 | B2 | 5/2009 | Brown et al. |
| 7,593,437 | B2 | 9/2009 | Staroudoumov et al. |
| 7,593,440 | B2 | 9/2009 | Spinelli et al. |
| 7,623,557 | B2 | 11/2009 | Tokuhisa et al. |
| 7,627,007 | B1 | 12/2009 | Armstrong et al. |
| 7,643,529 | B2 | 1/2010 | Brown et al. |
| 7,715,459 | B2 | 5/2010 | Brown et al. |
| 7,813,406 | B1 | 10/2010 | Nguyen et al. |
| 7,822,092 | B2 | 10/2010 | Ershov et al. |
| 7,920,616 | B2 | 4/2011 | Brown et al. |
| 7,948,673 | B2 | 5/2011 | Yoshimura et al. |
| 7,957,066 | B2 | 6/2011 | Armstrong et al. |
| 7,999,342 | B2 | 8/2011 | Hsu et al. |
| 8,208,505 | B2 | 6/2012 | Dantus et al. |
| 8,238,647 | B2 | 8/2012 | Ben-Yishay et al. |
| 8,298,335 | B2 | 10/2012 | Armstrong |
| 8,309,443 | B2 | 11/2012 | Tanaka et al. |
| 8,319,960 | B2 | 11/2012 | Aiko et al. |
| 8,391,660 | B2 | 3/2013 | Islam |
| 8,503,068 | B2 | 8/2013 | Sakuma |
| 8,629,384 | B1 | 1/2014 | Bieallak et al. |
| 8,665,536 | B2 | 3/2014 | Armstrong |
| 8,686,331 | B2 | 4/2014 | Armstrong |
| 8,755,417 | B2 | 6/2014 | Dribinski |
| 8,824,514 | B2 | 9/2014 | Armstrong |
| 8,873,596 | B2 | 10/2014 | Dribinski |
| 8,896,917 | B2 | 11/2014 | Armstrong |
| 8,929,406 | B2 | 1/2015 | Chuang et al. |
| 8,976,343 | B2 | 3/2015 | Genis |
| 2001/0000977 | A1 | 5/2001 | Vaez-Iravani et al. |
| 2002/0109110 | A1 | 8/2002 | Some et al. |
| 2002/0114553 | A1 | 8/2002 | Mead et al. |
| 2002/0191834 | A1 | 12/2002 | Fishbaine |
| 2003/0147128 | A1 | 8/2003 | Shafer et al. |
| 2003/0161374 | A1 | 8/2003 | Lokai |
| 2004/0080741 | A1 | 4/2004 | Marxer et al. |
| 2005/0041702 | A1* | 2/2005 | Fermann ................ G02F 1/39 372/25 |
| 2005/0110988 | A1 | 5/2005 | Nishiyama et al. |
| 2005/0111081 | A1 | 5/2005 | Shafer et al. |
| 2005/0128473 | A1 | 6/2005 | Karpol et al. |
| 2005/0157382 | A1 | 7/2005 | Kafka et al. |
| 2005/0254049 | A1 | 11/2005 | Zhao |
| 2005/0254065 | A1 | 11/2005 | Stokowski |
| 2006/0038984 | A9 | 2/2006 | Vaez-Iraani et al. |
| 2006/0171656 | A1 | 8/2006 | Adachi et al. |
| 2006/0239535 | A1 | 10/2006 | Takada |
| 2006/0291862 | A1 | 12/2006 | Kawai |
| 2007/0002465 | A1 | 1/2007 | Chuang et al. |
| 2007/0047600 | A1 | 3/2007 | Luo et al. |
| 2007/0103769 | A1 | 5/2007 | Kuwabara |
| 2007/0146693 | A1 | 6/2007 | Brown et al. |
| 2007/0211773 | A1 | 9/2007 | Gerstenberger et al. |
| 2007/0223541 | A1 | 9/2007 | Van Saarloos |
| 2007/0263680 | A1 | 11/2007 | Starodoumov et al. |
| 2007/0291810 | A1 | 12/2007 | Luo et al. |
| 2008/0182092 | A1* | 7/2008 | Bondokov ............ C30B 23/00 428/220 |
| 2008/0186476 | A1 | 8/2008 | Kusunose |
| 2008/0204737 | A1 | 8/2008 | Ogawa |
| 2009/0084989 | A1 | 4/2009 | Imai |
| 2009/0128912 | A1 | 5/2009 | Okada |
| 2009/0180176 | A1 | 7/2009 | Armstrong et al. |
| 2009/0185583 | A1 | 7/2009 | Kuksenkov et al. |
| 2009/0185588 | A1 | 7/2009 | Munroe |
| 2009/0296755 | A1 | 12/2009 | Brown et al. |
| 2010/0085631 | A1 | 4/2010 | Kusukame et al. |
| 2010/0188655 | A1 | 7/2010 | Brown et al. |
| 2010/0278200 | A1 | 11/2010 | Dicks et al. |
| 2011/0062127 | A1 | 3/2011 | Gu et al. |
| 2011/0073982 | A1 | 3/2011 | Armstrong et al. |
| 2011/0085149 | A1 | 4/2011 | Nathan |
| 2011/0101219 | A1 | 5/2011 | Uchiyama et al. |

(56) References Cited

U.S. PATENT DOCUMENTS

| | | | |
|---|---|---|---|
| 2011/0123163 A1 | 5/2011 | Muller et al. | |
| 2011/0134944 A1 | 6/2011 | Kaneda et al. | |
| 2011/0222565 A1 | 9/2011 | Horain et al. | |
| 2011/0228263 A1* | 9/2011 | Chuang | G01N 21/9501 356/300 |
| 2011/0279819 A1 | 11/2011 | Chuang et al. | |
| 2012/0026578 A1 | 2/2012 | Sakuma | |
| 2012/0033291 A1 | 2/2012 | Kneip | |
| 2012/0092657 A1 | 4/2012 | Shibata | |
| 2012/0113995 A1 | 5/2012 | Armstrong | |
| 2012/0120481 A1 | 5/2012 | Armstrong | |
| 2012/0137909 A1 | 6/2012 | Hawes et al. | |
| 2012/0314286 A1 | 12/2012 | Chuang et al. | |
| 2013/0016346 A1 | 1/2013 | Romanovsky et al. | |
| 2013/0021602 A1 | 1/2013 | Dribinski et al. | |
| 2013/0064259 A1 | 3/2013 | Wakabayashi et al. | |
| 2013/0077086 A1 | 3/2013 | Chuang et al. | |
| 2013/0088706 A1* | 4/2013 | Chuang | C30B 29/10 356/51 |
| 2013/0176552 A1 | 7/2013 | Brown et al. | |
| 2013/0194445 A1 | 8/2013 | Brown et al. | |
| 2013/0264481 A1 | 10/2013 | Chern et al. | |
| 2013/0313440 A1 | 11/2013 | Chuang et al. | |
| 2014/0016655 A1 | 1/2014 | Armstrong | |
| 2014/0050234 A1 | 2/2014 | Ter-Mikirtychev | |
| 2014/0071520 A1 | 3/2014 | Armstrong | |
| 2014/0111799 A1 | 4/2014 | Lei et al. | |
| 2014/0153596 A1 | 6/2014 | Chuang et al. | |
| 2014/0158864 A1 | 6/2014 | Brown et al. | |
| 2014/0204963 A1 | 7/2014 | Chuang et al. | |
| 2014/0226140 A1 | 8/2014 | Chuang et al. | |
| 2014/0291493 A1 | 10/2014 | Chuang et al. | |
| 2014/0305367 A1 | 10/2014 | Chuang et al. | |
| 2015/0007765 A1 | 1/2015 | Dribinski | |
| 2015/0177159 A1 | 6/2015 | Brown et al. | |
| 2015/0200216 A1 | 7/2015 | Muramatsu et al. | |
| 2015/0268176 A1 | 9/2015 | Deng | |
| 2015/0275393 A1* | 10/2015 | Bondokov | C30B 23/025 117/104 |
| 2015/0294998 A1 | 10/2015 | Nihtianov | |

FOREIGN PATENT DOCUMENTS

| | | |
|---|---|---|
| DE | 102009047098 A1 | 5/2011 |
| EP | 0532927 A2 | 3/1993 |
| EP | 0746871 | 5/2000 |
| EP | 0602983 | 6/2000 |
| EP | 1072938 A2 | 1/2001 |
| EP | 1194804 B1 | 7/2003 |
| EP | 1939917 | 7/2008 |
| EP | 2013951 A2 | 1/2009 |
| JP | H0511287 A | 1/1993 |
| JP | 2002-258339 A | 9/2002 |
| JP | 2003043533 A | 2/2003 |
| JP | 2006-60162 A | 3/2006 |
| JP | 2006071855 | 3/2006 |
| JP | 200786108 | 4/2007 |
| JP | 2007-206452 A | 8/2007 |
| JP | 2007298932 A | 11/2007 |
| JP | 2009-145791 A | 7/2009 |
| JP | 2010-54547 A | 3/2010 |
| JP | 2010-256784 A | 11/2010 |
| JP | 2011-23532 A | 2/2011 |
| JP | 2011-128330 A | 6/2011 |
| WO | 9532518 | 11/1995 |
| WO | 9617372 | 6/1996 |
| WO | 97/45902 | 2/1997 |
| WO | 03/069263 A1 | 8/2003 |
| WO | 2005/022705 A2 | 3/2005 |
| WO | 2009/082460 A2 | 7/2009 |
| WO | 2010/037106 A2 | 4/2010 |
| WO | 2012/154468 A2 | 11/2012 |
| WO | 2013/015940 A2 | 1/2013 |
| WO | 2014067754 | 5/2014 |

OTHER PUBLICATIONS

Mori et al.: "New Nonlinear Optical Crystal: Cesium Lithium Borate", Appl. Phys. Lett. 67, No. 13, Sep. 25, 1995, pp. 1818-1820.
Boyd, G. D. et al., "Parametric Interaction of Focused Gaussian Light Beams", Journal of Applied Physics, vol. 39, No. 8, Jul. 1968, 13 pages.
Lopez, L., et al., "Multimode squeezing properties of a confocal optical parametric oscillator: Beyond the thin-crystal approximation", Physical Review A 72, 013806 (2005 The American Physical Society), 10 pages.
KLA-Tencor Corporation, U.S. Apppl. No. 14/248,045, filed Apr. 8, 2014 and entitled "Passivation of Nonlinear Optical Crystals".
KLA-Tencor Corporation, U.S. Appl. No. 62/059,368, filed Oct. 3, 2014 and entitled "183nm Laser and Inspection System".
KLA-Tencor Corpoation, U.S. Appl. No. 14/210,355, filed Mar. 13, 2014 and entitled "193nm Laser and an Inspection System Using a 193nm Laser".
Raoult, F. et al., "Efficient generation of narrow-bandwidth picosecond pulses by frequency doubling of femtosecond chirped pulses", Jul. 15, 1998 / ol. 23, No. 14 / Optics Letters, pp. 1117-1119.
Saikawa et al., "52 mJ narrow-bandwidth degenerated optical parametric system with a large-aperture periodically poled MgO:LiNbO3 device", Optics Letters, 31 (#21), 3149-3151 (2006).
Sakuma et al., "True CW 193.4-nm light generation based on frequency conversion of fiber amplifiers", Optics Express 19 (#16), 15020-15025 (2011).
Sakuma et al., "High power, narrowband, DUV laser source by frequency mixing in CLBO", Advanced High-Power Lasers and Applications, Nov. 2000, pp. 7-14, Ushio Inc.
Mead et al., "Solid-state lasers for 193-nm photolithography", Proc. SPIE 3051, Optical Microlithography X, pp. 882-889 (Jul. 7, 1997).
Zavartsev et al. "High efficient diode pumped mixed vanadate crystal Nd:Gd0.7Y0.3VO4 laser", International Conference on Lasers, Applications, and Technologies 2007: Advanced Lasers and Systems, Valentin A. Orlovich et al. ed., Proc. of SPIE vol. 6731, 67311P (2007), 5 pages.
International Search Report and Written Opinion dated May 13, 2014 for PCT/US2014/012902 (P4060-PCT), filed Jan. 24, 2014 in the name of KLA-Tencor Corporation.
Dianov et al. "Bi-doped fiber lasers: new type of high-power radiation sources", Conference on Lasers and Electro-Optics, May 6-11, 2007, 2 pages.
Kalita et al. "Multi-watts narrow-linewidth all fiber Yb-doped laser operating at 1179 nm", Optics Express, 18 (6), pp. 5920-5925 (2010).
Kashiwagi et al. "Over 10W output linearly-polarized single-stage fiber laser oscillating above 1160 nm using Yb-doped polarization-maintaining solid photonic bandgap fiber", IEEE Journal of Quantum Electronics, 47 (8), pp. 1136-1141 (2011).
Sasaki et al. "Progress in the growth of a CsLiB6O10 crystal and its application to ultraviolet light generation", Optical Materials, vol. 23, 343-351 (2003).
Shirakawa et al. "High-power Yb-doped photonic bandgap fiber amplifier at 1150-1200nm", Optics Express 17 (2), 447-454 (2009).
Ter-Mikirtychev et al. "Tunable LiF:F2- color center laser with an intracavity integrated-optic output coupler", Journal of Lightwave Technology, 14 (10), 2353-2355 (1996).
Yoo et al. "Excited state absorption measurement in bismuth-doped silicate fibers for use in 1160 nm fiber laser", 3rd EPS-QEOD Europhoton Conference, Paris, France, Aug. 31-Sep. 5, 2008, 1 page.
International Search Report and Written Opinion dated Jul. 11, 2014 for PCT/US2014/030989 (P4128-PCT), filed Mar. 18, 2014 in the name of KLA-Tencor Corporation.
International Search Report and Written Opinion dated May 20, 2014 for PCT/US2014/016198 (P4102-PCT), filed Feb. 13, 2014 in the name of KLA-Tencor Corporation.
KLA-Tencor Corporation, U.S. Appl. No. 14/248,045, filed Apr. 8, 2014 and entitled "Passivation of Nonlinear Optical Crystals".
KLA-Tencor Corpoation, US. Appl. No. 14/210,355, filed Mar. 13, 2014 and entitled "193nm Laser and an Inspection System Using a 193nm Laser".
Herriott, et al., "Folded Optical Delay Lines", Applied Optics 4, #8, pp. 883-889 (1965).

(56) References Cited

OTHER PUBLICATIONS

Herriott, et al., "Off-Axis Paths in Spherical Mirror Interferometers", Applied Optics 3, #4, pp. 523-526 (1964).

Stevanovic et al., A CMOS Image Sensor for High-Speed Imaging:, 2000 IEEE int'l. Solid-State Circuits Conf., 3 pgs.

Paetzel et al., "Activation of Silicon Wafer by Excimer Laser", 18th IEEE Conf. Advanced Thermal Processing of Semiconductors-RTP 2010, 5 pgs.

Huang et al., "Back-Side Illuminated Photogate CMOS . . .", IEEE Sensors Journal, vol. 11, No. 9, Sep. 2011, 5 pgs.

Niclass et al., "Design and Characterization of a CMOS 3-D . . .", IEEE Journal Solid-State Circuits, vol. 40, No. 9, Sep. 2005, 8 pgs.

Xiaogian, Fu, "Higher Quantum Efficiency by Optimizing . . .", 978-1-4244-6644-3/10 IEEE, pp. 234-235.

Itzler, et al., "InP-based Geiger-mode . . .", Proc. SPIE vol. 7320 (2000), 12 pgs.

Sarubbi et al., "Pure boron-doped photodiodes . . .", IEEE, Sep. 15, 2008, pp. 278-281.

Dulinski, "Tests of a backside illuminated monolithic CMOS pixel . . .", Nuclear Instruments and Methods in Physics Research A 546 (2005) 274-280, 7 pgs.

Sakic, Agata, "Boron-layer silicon photodiodes for high-efficiency low-energy electron detection", Solid-State Electronics 65-66 (2011), pp. 38-44.

Omatsu, Takashige et al., "High repetition rate Q-switching performance in transversely diode-pumped Nd doped mixed gadolinium yttrium vanadate bounce laser", Optics Express vol. 14, Issue 7, pp. 2727-2734, Apr. 3, 2006.

\* cited by examiner

MULTI-STAGE RAMP-UP ANNEALING FOR FREQUENCY-CONVERSION CRYSTALS

RELATED APPLICATION

The present application is a divisional of U.S. Application Ser. No. 14/507,758, entitled "Laser With High Quality, Stable Output Beam, And Long Life High Conversion Efficiency Non-Linear Crystal", and filed Oct. 6, 2014, which is a divisional of U.S. application Ser. No. 13/412,564, entitled "Laser With High Quality, Stable Output Beam, And Long Life High Conversion Efficiency Non-Linear Crystal", and filed Mar. 5, 2012, now U.S. Pat. No. 8,873,596, and claims priority of U.S. Provisional Application 61/510,633, entitled "Mode-Locked UV Laser With High Quality, Stable Output Beam, Long-Life High Conversion Efficiency Non-Linear Crystal And A Wafer Inspection Using A Mode-Locked UV Laser", and filed on Jul. 22, 2011.

BACKGROUND OF THE INVENTION

1. Field of the Invention

The present invention relates to lasers and in particular to lasers using non-linear crystals to obtain shorter wavelength radiation from the longer wavelength radiation by a frequency-conversion process.

2. Related Art

Each successive node of semiconductor manufacturing requires detection of smaller defects and particles on the wafer. Therefore, yet higher power and shorter wavelength UV (ultraviolet) lasers for wafer inspection are always in demand. Because the defect or particle size is reduced, the fraction of the light reflected or scattered by that defect or particle is also typically reduced. As a result, an improved signal-to-noise ratio is required to detect smaller defects and particles. If a brighter light source is used to illuminate the defect or particle, then more photons will be scattered or reflected and the signal-to-noise ratio can be improved as long as other noise sources are controlled. Using shorter wavelengths can further improve the sensitivity to smaller defects, because the fraction of light scattered by a particle smaller than the wavelength of light increases as the wavelength decreases.

In general, semiconductor wafer inspection and metrology needs can be met by continuous wave (CW) lasers with high beam quality (e.g. with $M^2$ close to 1, wherein $M^2$ is the ratio of the beam parameter product of the beam to that of an ideal Gaussian beam of the same wavelength). If CW lasers of sufficient power and beam quality are not available, then the next best alternative is generally a high repetition rate laser, e.g. with a repetition rate of approximately 50 MHz or higher. Such high repetition rates are possible with mode-locked lasers (which is a type of pulsed laser). Q-switched lasers have repetition rates that are much lower (lower than 10 MHz, usually lower than 1 MHz). Generally, mode-locked lasers are capable of emitting extremely short pulses on the order of picoseconds or even femtoseconds. A mode-locked laser induces a fixed phase relationship between the modes of its resonant cavity such that interference between those modes causes the laser light to be produced as pulses.

Beam quality (e.g. as measured by $M^2$) is important in semiconductor inspection and metrology applications because a laser beam must be focused to a small spot (or line) to detect small defects or particles and/or to measure small areas. If the beam quality is poor, then the focused spot (or line) on the wafer is not Gaussian in profile and the tails of that profile contain more energy than ideal. Those bigger tails result in at least some of the signal being collected from outside the area of interest, thereby reducing the contrast of the signal from the area of interest.

Non-linear crystals can be used to create a UV laser beam by generating a harmonic of a long wavelength beam or by mixing two laser beams of different frequencies to create a frequency equal to the sum (or difference) of the two frequencies. Because the harmonic generation and the mixing process are non-linear processes, higher incident power density typically results in a more efficient conversion process and higher output power.

However, increasing the incident laser power on a non-linear crystal can have undesirable side effects. Specifically, a high power level may change the refractive index of the crystal (photorefraction). Because the focused laser spot in the crystal has an approximately Gaussian profile, the intensity is different at different locations within the crystal. Therefore, the change in the refractive index varies with location in the crystal. This refractive index gradient in the crystal can distort the output beam, thereby resulting in astigmatism. As the quality of the output laser beam worsens, the spot or the line on the wafer generated by that beam becomes broader and thus less efficient for detecting small particles or defects. Although small amounts of astigmatism may be approximately corrected by optics placed in the beam path after the crystal, such correction will only be approximate and will only be effective if the initial astigmatism level is very low.

Another undesirable side effect of higher incident power level on the crystal is that permanent damage may occur in the crystal over time. With accumulated exposure, this damage can result in generally decreasing power intensity as well as generally increasing astigmatism. Therefore, correcting the astigmatism with optics would require frequent compensating adjustments, which would be impractical in commercial applications. Moreover, the astigmatism may also rapidly increase to the level where accurate compensation is not possible even with adjustment.

Generating a shorter output wavelength can also accelerate the degradation of the crystal because the output photons are more energetic and therefore can change characteristics of, or even permanently damage, the crystal. Thus, at shorter output wavelengths, astigmatism and other adverse beam quality and intensity effects may also increasingly occur.

The optimum power density in the non-linear crystal is a balance between maximum conversion efficiency (which usually requires as high a power density as possible), and minimizing color center formation, photorefraction, and two-photon absorption (all of which are minimized by lowering the power density) while maintaining a good beam profile.

Notably, photorefraction and two-photon absorption may cause a temporary change in optical properties, which persists for at least the duration of the incident laser pulse and, typically, for a short time thereafter. When the laser repetition rate is low, as in a Q-switched laser, there may be sufficient time between one pulse and the next for these changes to the crystal to partially or fully relax back to the original state. This relaxation may be faster if the crystal is operating at a high temperature (such as between 120-150° C., which is a typical temperature range for standard operation). Applications in the semiconductor inspection and metrology typically are better served by very high repetition rates (such as 50 MHz, 100 MHz, or higher) as can be achieved by mode-locked lasers. However, such high repetition rates typically do not allow time for the changes in crystal properties to relax substantially from one pulse to the next.

Non-linear crystals, such as CLBO (cesium lithium borate) or CBO (cesium borate), can be used to create deep UV light from the $2^{nd}$ harmonic of a visible laser light input. For example, 266 nm wavelength light can be created from a 532 nm laser beam using CLBO. In another embodiment, light near 213 nm wavelength can be created by mixing, for example, 266 nm and 1064 nm wavelengths. The maximum power level at which such crystals can be operated is limited by defects and impurities in the crystals.

Impurities in a crystal or defects in its crystal lattice can degrade the lifetime of the crystal or create color centers that become locations at which changes in the crystal optical properties happen faster than elsewhere in the crystal. Thus, to the extent possible, the highest purity of starting material should be used for fabricating the crystal.

Notably, impurities, such as water, can be incorporated into a crystal during its growing process or even during normal operation (when used in an inspection system) even if not present in the starting material. These impurities can adversely impact the crystal lifetime at high power densities. Unfortunately, improving the purity of the starting material does not reduce impurities that are incorporated during operation.

One known technique for reducing or slowing deterioration in the crystal is to operate the crystal at a high temperature (typically between 120-150° C.), which generates higher energy electrons in the crystal. These higher energy electrons are able to move around more easily, thereby cancelling out some of the light-induced changes in the short term. This technique is most useful for low repetition rate lasers because there is a relatively long time interval between pulses (which allows recovery from the effects of one pulse). This high operating temperature can also help prevent absorption of water by the crystal while it is in use.

Although operating the crystal at a high temperature can provide more electrons with high enough mobility to neutralize some changes in the crystal, it also increases the energy of defect states in the crystal. Thus, the high operating temperature can slow some defect mechanisms while accelerating others. Notably, the increased temperature is less effective at reducing short-term changes in the crystal when the repetition rate is high.

Another known technique to deal with crystal damage is to use one location in the crystal for a period of time, then move to a new location before there is too much degradation of the output beam quality and/or intensity. Frequent adjustment of the location in the crystal used for frequency conversion means that for a significant fraction of the operating time, the laser is being adjusted, realigned, or is stabilizing after an adjustment. Even if the adjustment and realignment are automated, there may be times when the laser is not operating to full specification while it stabilizes after adjustment. In inspection and measurement applications in industries like the semiconductor industry where manufacturing facilities run 24 hours a day, this interruption to, or reduction in, operating time is a significant disadvantage. If the damage rate is high, even with frequent and automatic adjustments of the conversion location in the crystal, the crystal may still last only a few days or a few weeks before needing to be replaced. Such a short time interval between service events is unacceptable in the semiconductor industry.

Therefore, a need arises for a high power laser system that includes a frequency-conversion crystal (i.e. a non-linear crystal capable of generating harmonics of the fundamental laser wavelength), yet can ensure a high quality, stable laser beam and a long crystal lifetime.

SUMMARY OF THE INVENTION

A mode-locked laser system operable at low temperature is described. As used herein, a "low" temperature is approximately 50° C. and below (wherein a conventional standard operating temperature is at least 100° C., and typically between 120° C.-150° C.). In one embodiment, the low temperature may be between 30° C. and −10° C. This laser system can include an annealed, frequency-conversion crystal and a housing to protect the crystal from impurities during standard operation at the low temperature, and thereby maintain the annealed condition of the crystal. In general, the crystal has a length approximately equal to the smaller of twice the Rayleigh range in a non-walk-off direction and a length of twice a beam waist radius in a walk-off direction divided by a walk-off angle in radians. In one embodiment, the crystal can have an increased length (such as 12.5 mm-long or 15 mm-long CLBO compared with a typical 10 mm-long CLBO used for converting 532 nm to 266 nm). First beam shaping optics can be configured to focus a beam from a light source to an elliptical cross section at a beam waist located in or proximate to the crystal. A harmonic separation block can divide an output from the crystal into beams of different frequencies separated in space. In one embodiment, the mode-locked laser system can further include second beam shaping optics configured to convert an elliptical cross section of the desired frequency beam into a beam with a desired aspect ratio, such as a circular cross section.

In one embodiment, the elliptical cross section in the crystal can have an aspect ratio between 2:1 and 6:1. The first beam shaping optics can include at least one of a prism, a cylindrical curvature element, a radially-symmetric curvature element, and a diffractive element. The harmonic separation block can include a prism, such as a Pellin-Broca prism. The crystal can be a CLBO (cesium lithium borate) crystal, a CBO (cesium borate) crystal, a BBO (β barium borate) crystal, an LBO (lithium triborate) crystal, a lithium niobate crystal, a KDP (potassium dihydrogen phosphate) crystal or another non-linear optical crystal.

A method of operating a laser system at low temperature is also described. In this method, a beam from a light source can be focused into an elliptical cross section at a beam waist in or proximate to an annealed, frequency-conversion crystal. From an output of the crystal, a desired frequency beam can be separated from any undesired frequency beam. The method can further include maintaining an annealed condition of the crystal during standard operation at the low temperature and/or converting the elliptical cross section into a circular cross section.

A method of annealing a frequency-conversion crystal is also described. In this method, the temperature of the crystal can be increased to about 150° C. over about 2 hours. The temperature can be held near 150° C. for about 10 hours. Then, the temperature can be increased to about 200° C. over about 1 hour. At this point, the temperature can be held between 150-200° C. for about 100 hours. Finally, the temperature can be decreased down to room temperature over about 3 hours.

Another method of annealing a frequency-conversion crystal is also described. In this method, during the first annealing step described above, a determination is made whether —OH bonds absorption is at a first level. If not, then the temperature is continued to be held near 150° C. If so, then the temperature is increased to about 200° C. over about 1 hour. During the second annealing step described above, a determination is made whether the —OH bonds absorption is at a second level. If not, then the temperature is continued to be held between 150-200° C. If so, then the temperature is decreased down to room temperature over about 3 hours. In one embodiment, determining absorption can be performed using FTIR (Fourier transform infrared spectroscopy). For example, FTIR can monitor the —OH bonds near 3580 $cm^{-1}$ in an infra-red spectrum.

A multi-stage ramp-up annealing process is also described. In this process, a first ramp-up stage can increase a temperature to a first predetermined temperature. The temperature can be held at the first predetermined temperature for a first predetermined period. Then, a second ramp-up stage can increase the temperature to a second predetermined temperature, the second predetermined temperature being higher than the first predetermined temperature. The temperature can be held at the second predetermined temperature for a second predetermined period. Finally, the temperature can be decreased to room temperature.

Another multi-stage ramp-up annealing process is also described. In this process, a first ramp-up stage can increase a temperature to a first predetermined temperature. The temperature can be held at the first predetermined temperature until —OH bonds absorption is at a first level. Then a second ramp-up stage can increase the temperature to a second predetermined temperature, which is higher than the first predetermined temperature. The temperature can be held at the second predetermined temperature until the —OH bonds absorption is at a second level. Finally, the temperature can be decreased to room temperature.

An optical system for detecting contaminants and defects on a test surface is also described. This optical system can include the improved laser system for generating a laser beam and optics directing the laser beam along a path onto the test surface, and producing an illuminated spot thereon. A detector and ellipsoidal mirrored surface are also provided. The mirrored surface and detector have an axis of symmetry about a line perpendicular to the test surface. The mirrored surface defines an input aperture positioned proximate to the test surface to receive scattered light there through from the surface and an exit aperture. The mirrored surface is substantially rotationally symmetric about the axis of symmetry, so that the mirrored surface reflects and focuses rotationally symmetrically about the axis of symmetry light that passes through the input aperture to the detector. The exit aperture is located opposite to the input aperture.

An optical system for detecting anomalies of a sample is also described. This optical system can include the improved laser system for generating first and second beams. First optics can direct the first beam of radiation along a first path onto a first spot on a surface of the sample. Second optics can direct the second beam of radiation along a second path onto a second spot on a surface of the sample. The first and second paths are at different angles of incidence to said surface of the sample. Collection optics can include a curved mirrored surface for receiving scattered radiation from the first or the second spot on the sample surface and originating from the first or second beam and focusing the scattered radiation to a first detector. The first detector can provide a single output value in response to the radiation focused onto it by said curved mirrored surface. An instrument can cause relative motion between the two beams and the sample so that the spots are scanned across the surface of the sample.

A surface inspection apparatus is also described. This apparatus can include the improved laser system for generating a beam of radiation. An illumination system can be configured to focus the beam of radiation at a non-normal incidence angle relative to a surface to form an illumination line on the surface substantially in a plane of incidence of the focused beam. The plane of incidence is defined by the focused beam and a direction that is through the focused beam and normal to the surface. A collection system can be configured to image the illumination line. The collection system can include an imaging lens for collecting light scattered from a region of the surface comprising the illumination line, a focusing lens for focusing the collected light, and a device comprising an array of light sensitive elements. Each light sensitive element of the array of light sensitive elements can be configured to detect a corresponding portion of a magnified image of the illumination line.

A pulse multiplier including the improved laser system for generating an input laser pulse is also described. This pulse multiplier can further include a polarizing beam splitter that receives the input laser pulse. A wave plate can receive light from the polarized beam splitter and generate a first set of pulses and a second set of pulses, the first set of pulses having a different polarization than the second set of pulses. A set of mirrors can create a ring cavity including the polarizing beam splitter and the wave plate. The polarizing beam splitter can transmit the first set of pulses as an output of the pulse multiplier and reflect the second set of pulses into the ring cavity.

DETAILED DESCRIPTION OF THE DRAWINGS

Figure 1A:
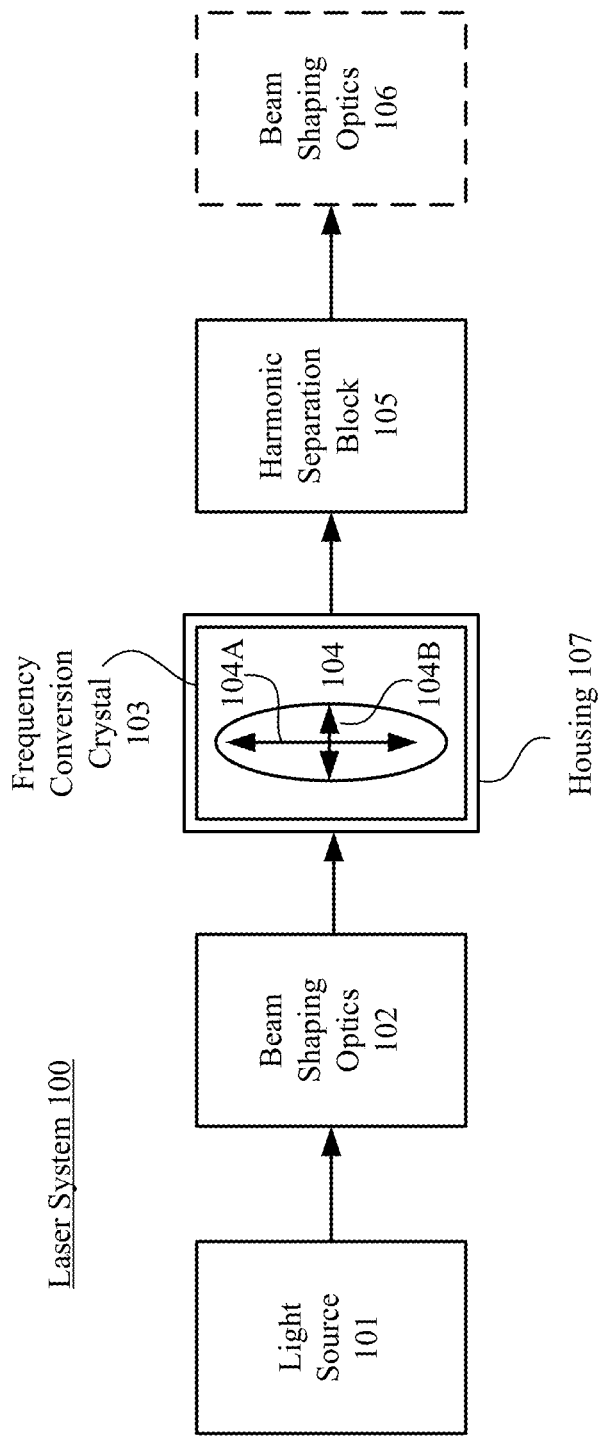
FIG. 1A illustrates a simplified, laser system in accordance with the present invention.

In accordance with an improved laser system and operation, a mode-locked laser system includes an annealed, frequency-conversion crystal and an input light source that creates an elliptical cross-section beam waist located in or proximate to the crystal during normal operation. In some embodiments, the frequency-conversion crystal is maintained at a low temperature. As used herein, a "low" temperature is approximately 50° C. and below. In one embodiment, the low temperature may be between 30° C. and −10° C. This combination of components and operation can ensure beam quality, beam stability, and crystal lifetime.

In accordance with some embodiments of a laser system, a "long" crystal (described below) can be included. In a typical frequency conversion stage in a laser, the input laser beam is focused to an approximately circular cross section beam waist in or proximate to the frequency-conversion crystal. The longer the crystal, the more of input wavelength(s) will be converted to the output wavelength because the input laser beam spends more time inside the crystal. However, too long a crystal degrades the beam quality because of walk-off between the input and output wavelengths. One factor determining the maximum useable conversion crystal length is the walk-off angle (which depends on the crystal material and the input and output wavelengths) and the beam diameter. In applications for inspection and measurement of semiconductors, good beam quality is required, so typically the maximum useable crystal length is approximately equal to the laser beam-waist diameter divided by the walk-off angle in radians. Expressed as an equation, if the radius of the beam waist is $w_0$, the walk-off angle in radians is $\alpha_{w_0}$, and the crystal length L, then the maximum useable crystal length is approximately given by:

$$L_{max} \approx \frac{2w_0}{\alpha_{w_0}}$$

For example, for conversion of a 532 nm input laser beam to 266 nm in a CLBO crystal, the walk-off angle is approximately 33 mrad (with a weak dependence on operating temperature). If the beam waist radius were approximately 175 μm, then the maximum crystal length would be approximately 11 mm. A 10 mm CLBO crystal length would typically be used for such an application. Although increasing the beam waist radius would allow a longer crystal to be used, the overall conversion efficiency would be reduced because the conversion efficiency per unit length depends on the power density which scales inversely with the square of $w_0$.

Very small values of of $w_0$ are generally not desirable because too high a power density damages the crystal rapidly. Furthermore, small values of $w_0$ reduce the Rayleigh range of the focused laser beam so making the system more sensitive to misalignment, and, if the crystal length is greater than about twice the Rayleigh range, result in only a part of the crystal length being efficiently used for frequency conversion. The Rayleigh range of a laser beam with an approximately cross-section beam and good beam quality (i.e. $M^2$ close to 1.0 as discussed below) is given by:

$$R = \frac{\pi w_0^2}{\lambda}$$

Often the crystal length is chosen to be approximately equal to the smaller of twice the Rayleigh range and $L_{max}$ above, if large enough crystals of good enough quality are available at a reasonable cost. Thus, in general, the crystal has a length approximately equal to a smaller of twice a Rayleigh range and a length of twice a beam waist radius divided by a walk-off angle in radians.

In some embodiments of the invention, the beam is focused into an elliptical cross section at the beam waist in or proximate to the crystal, as described below. The ellipse is elongated in the walk-off direction relative to the non-walk-off direction. An increased beam waist radius in the walk-off direction allows a longer crystal to be used since $L_{max}$ depends only on the value of $w_0$ in the walk-off direction.

The power density at an elliptical focus is inversely proportional to the product of the beam waist radii (or inversely proportional to the beam waist radius squared for a circular cross-section beam waist). Instead of a circular focus, it is possible to use an elliptical focus with two beam waist radii chosen such that the power density is substantially equivalent to that of the circular focus, resulting in conversion efficiency per unit length and damage rate being substantially similar between the circular and elliptical focus cases. However, because the elliptical focus has a larger beam waist radius in the walk-off direction, the crystal length may be longer resulting in an overall conversion efficiency increase. Alternatively, the elliptical focus beam waist radii could be chosen so as to slightly reduce the power density (for example to approximately 70% of the power density of the circular beam waist) so as to reduce the rate of damage to the crystal, while using a long enough crystal (twice as long in this example) to result in substantially equal overall conversion efficiency. Note also that if the ellipse has too large an aspect ratio, then the smaller $w_0$ value in the more tightly focused direction will lead to a smaller Rayleigh range in that direction and so limit the maximum useful crystal length. One skilled in the appropriate art would understand these and other trade-offs between overall conversion efficiency, damage rate, crystal length and cost, and can select an appropriate beam waist profile.

Since the beam waist radius in the non-walk-off direction is smaller than the walk-off beam waist radius when an elliptical focus is used in accordance with embodiments of the present invention, the Rayleigh range in the non-walk-off direction is shorter than the Rayleigh range in the walk-off direction. Therefore, the maximum useful crystal length is approximately determined by the smaller of twice the Rayleigh range in the non-walk-off direction and the length defined by twice a beam waist radius in the walk-off direction divided by a walk-off angle in radians.

For example, in a frequency conversion stage that converts 532 nm to 266 nm using a CLBO crystal, instead of a circular beam waist of approximately 175 μm in radius, an elliptical beam waist of approximately 125 μm in radius (non-walk-off direction) by 250 μm in radius (walk-off direction) could be used. The power density in these two cases is substantially similar, but the elliptical focus would allow a maximum crystal length of approximately 15 mm, versus a maximum crystal length of approximately 11 mm for the circular focus. The overall conversion efficiency would be about 50% greater for the elliptical focus if used with the longer crystal.

FIG. 1A illustrates a simplified, improved laser system 100. In laser system 100, the output of a light source 101 can be focused to an elliptical cross-section Gaussian beam waist in or proximate to a frequency-conversion crystal 103 (also called crystal 103 for ease of reference) using beam shaping optics 102. As used herein, the term "proximate to" is preferably less than half of the Rayleigh range from the center of crystal 103. Note that crystal 103 may be a long crystal, as discussed above, or a standard-sized crystal. In one preferred embodiment, the aspect ratio between the Gaussian widths of the principle axes of the ellipse could be between about 2:1 and about 6:1. Note that the principle axes 104A and 104B of an ellipse 104 are perpendicular to one another and define the longest length and the widest width of ellipse 104. In other preferred embodiments the ratio between the principle axes of the ellipse could be between about 2:1 and about 10:1. In one embodiment, the wider Gaussian width is substantially aligned with the walk-off direction of the frequency-conversion crystal (e.g. to within about 10° of alignment).

Figure 1B:
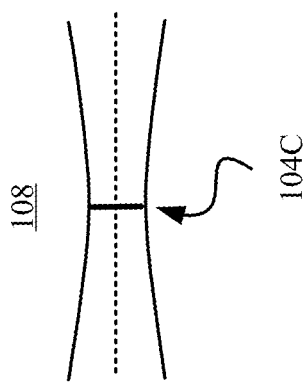
FIG. 1B illustrates an exemplary Gaussian laser beam with beam waist indicated.
Figure 1D:
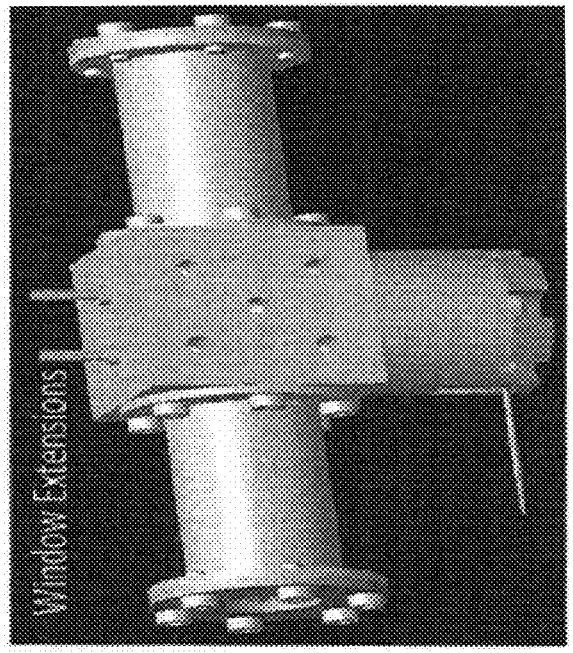
FIGS. 1C, 1D, and 1E illustrate exemplary housings that could implement a housing for protecting the frequency-conversion crystal from impurities, thereby maintaining the annealed condition of the crystal whether the laser is operating or not operating.
Figure 1E:
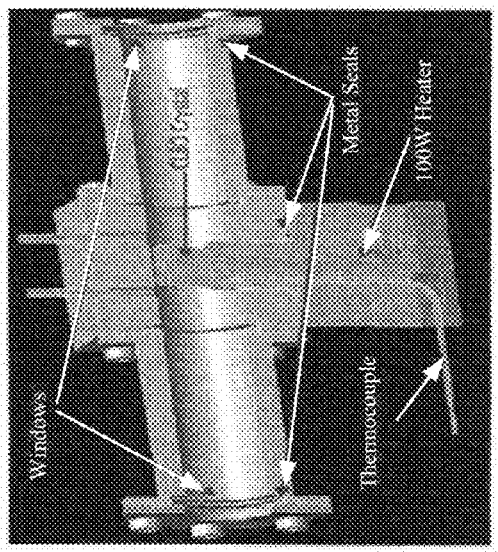
Figure 1C:
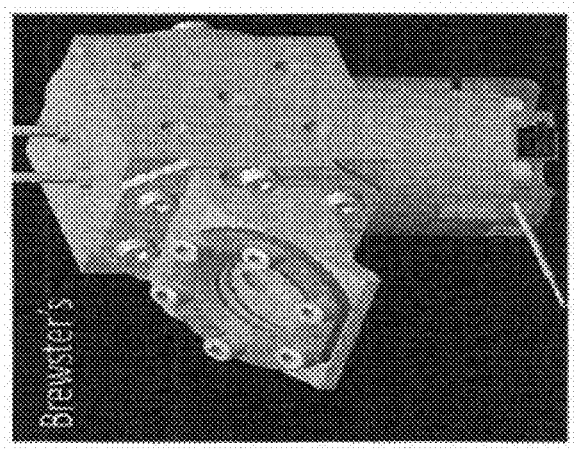

FIG. 1B illustrates an exemplary Gaussian laser beam 108 (with exaggerated tails for clarity), wherein line 104C indicates a 2× beam waist (also called a focal region). FIGS. 1C, 1D, and 1E illustrate exemplary housings that could implement housing 107, which can protect frequency-conversion crystal 103 during standard operation. In one embodiment, housing 107 can protect crystal 103 from impurities, thereby facilitating maintaining its annealed condition even with a low standard operating temperature, i.e. less than about 50° C. Note that a crystal exposed to impurities over time will begin to deteriorate and may revert back to substantially an unannealed state. U.S. patent application Ser. No. 12/154,337, entitled "Enclosure For Controlling The Environment of Optical Crystals", filed May 6, 2008, describes these housings in greater detail, and is incorporated by reference herein. In other embodiments, housing 107 may be a larger structure including crystal 103 and other components of a laser system. In one embodiment, housing 107 is large enough to house all components of the laser system. Note that the larger the housing, the more precautions needed for maintenance and repair of the laser system (to protect crystal 103 from degradation and maintain its annealed condition). Therefore, in one embodiment, housing 107 is preferably smaller, rather than larger.

Beam shaping optics 102 can include anamorphic optics, which can change the cross section of output from light source 101. Anamorphic optics can include, for example, at least one of a prism, a cylindrical curvature element, a radially-symmetric curvature element, and a diffractive element. In one embodiment, light source 101 can include a laser producing a frequency in the visible range, e.g. 532 nm, to be doubled inside crystal 103. In other embodiments, light source 101 can include a laser source producing two or more frequencies to be combined inside crystal 103 to generate a sum or difference frequency.

Figure 1F:
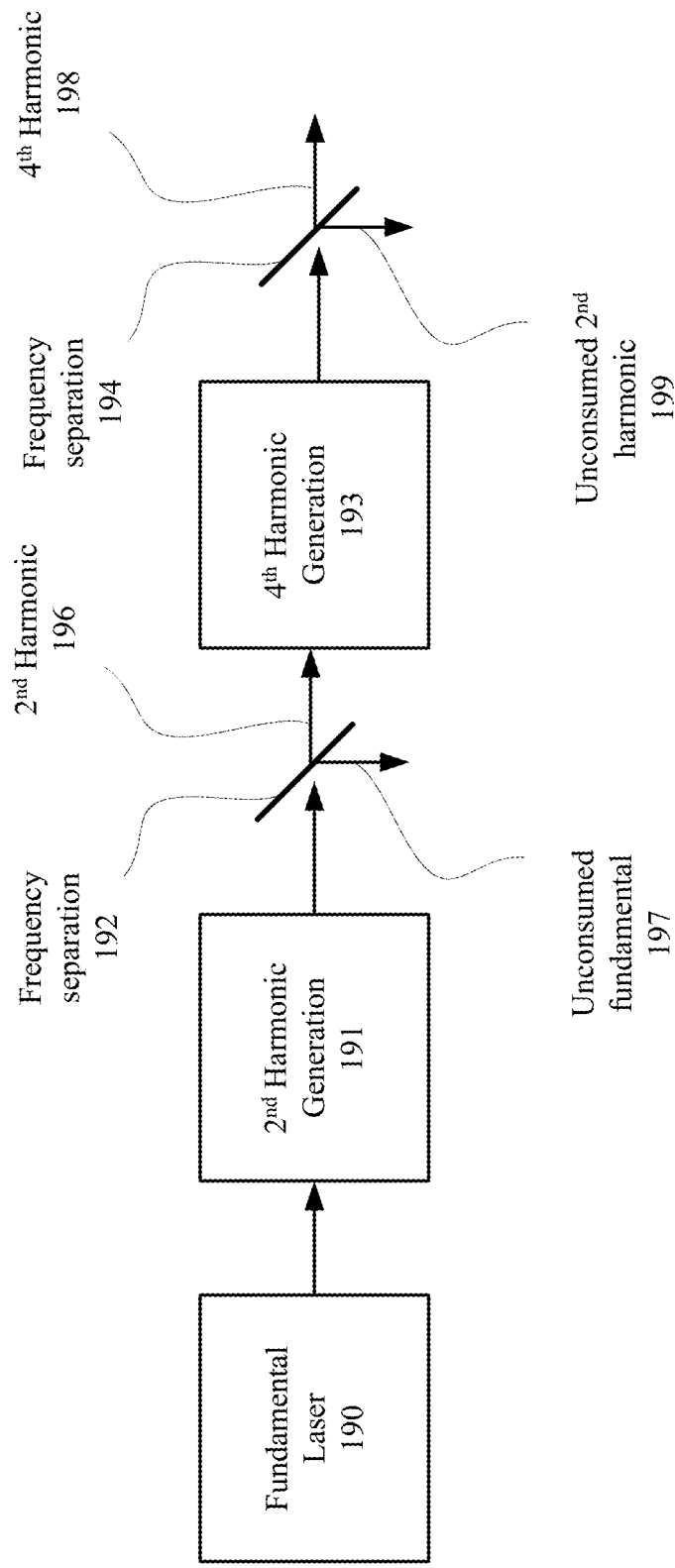
FIG. 1F illustrates an exemplary multi-step frequency conversion.

FIG. 1F illustrates an exemplary frequency conversion that generates a $4^{th}$ harmonic generation from, for example, a 1064 nm fundamental wavelength. The fundamental wavelength, which is generated by a laser 190, can be converted to a $2^{nd}$ harmonic 196 (i.e. 532 nm wavelength) using a $2^{nd}$ harmonic generation technique 191 and a frequency separation technique 192. Frequency separation technique 192 can separate the unwanted fundamental (i.e. an unconsumed fundamental 197) from $2^{nd}$ harmonic 196. In one embodiment, $2^{nd}$ harmonic generation technique 191 and frequency separation technique 192 can be implemented using the above-described beam shaping optics 102, frequency conversion crystal 103, and harmonic separation block 105.

$2^{nd}$ harmonic 196, in turn, can be the source for a $4^{th}$ harmonic 198 (i.e. 266 nm wavelength), which can be created by using a $4^{th}$ harmonic generation technique 193 and a frequency separation technique 194. Frequency separation technique 194 separates an unwanted $2^{nd}$ harmonic, i.e. unconsumed $2^{nd}$ harmonic 199, from $4^{th}$ harmonic 198. In one embodiment, $4^{th}$ harmonic generation technique 193 and frequency separation technique 194 can be implemented using the above-described beam shaping optics 102, frequency conversion crystal 103, and harmonic separation block 105. In another embodiment, more than one of the frequency conversion and separation stages (such as the $2^{nd}$ and $4^{th}$ harmonic conversion stages in the example) can be implemented using the above-described beam shaping optics 102, frequency conversion crystal 103, and harmonic separation block 105.

Note that the exemplary frequency conversion of FIG. 1F is illustrative only and not a limitation. Other harmonics may be created by, for example, mixing the fundamental with the $2^{nd}$ harmonic to create a $3^{rd}$ harmonic, or mixing the fundamental with the $4^{th}$ harmonic (or mixing $2^{nd}$ and $3^{rd}$ harmonics) to create a $5^{th}$ harmonic. Any, or all, of the conversion stages that generate ultraviolet (UV) wavelengths can use the beam shaping optics, the frequency conversion crystal, and the harmonic separation block. Note that although FIG. 1F is drawn as if the harmonic separation blocks reflect the unwanted frequencies and the wanted frequencies travel substantially undeviated, this is merely an illustration that harmonic separation blocks separate the frequencies and not meant to limit which frequencies are reflected or transmitted.

Figure 2A:
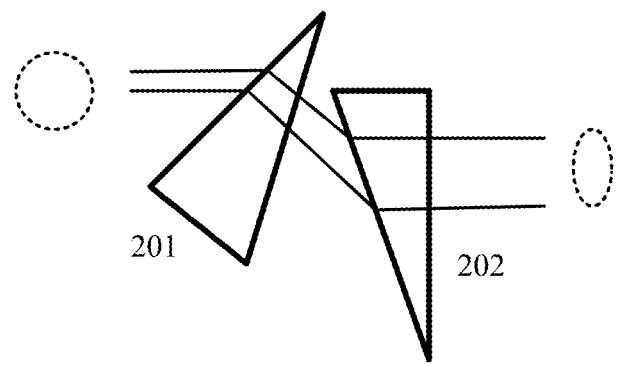
FIGS. 2A, 2B, and 2C illustrate exemplary anamorphic optics for creating an elliptical cross section of a light source output.
Figure 2B:
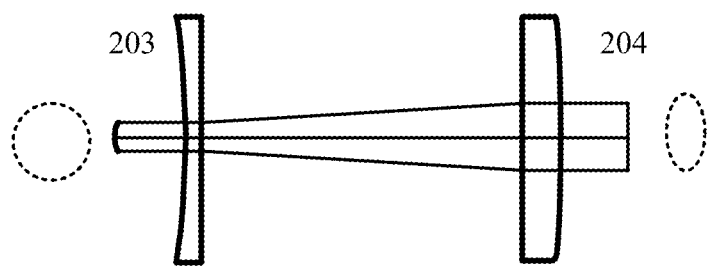
Figure 2C:
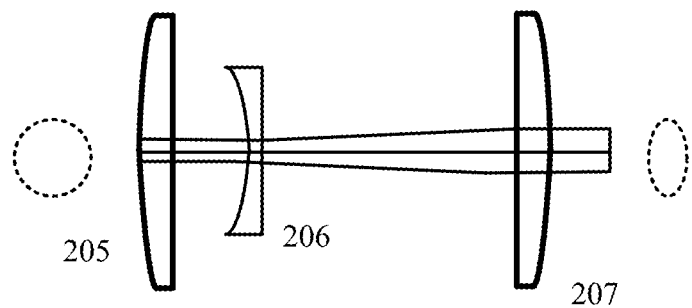

FIGS. 2A, 2B, and 2C illustrate exemplary anamorphic optics. FIG. 2A illustrates two prisms 201 and 202 that can be configured to operate near Brewster's angle. In one embodiment, prisms 201 and 202 can be tuned to adjust the ellipticity of the beam without introducing any power in the system. FIG. 2B illustrates a cylindrical telescope implemented with two lenses 203 and 204. Note that in a cylindrical telescope, collimation can be set to compensate for most astigmatism. FIG. 2C illustrates an afocal cylindrical zoom telescope implemented with three lenses 205, 206, and 207. An afocal cylindrical zoom telescope can be used to tune the beam diameter and set focusing. Note that although the anamorphic optics of FIGS. 2A, 2B, and 2C include two or three components, other embodiments may include any number of components. Indeed, the optics configurations of FIGS. 2A-2C are illustrative only and not limiting. Referring back to FIG. 1, beam shaping optics 102 generate an elliptical cross section beam output, which can then be focused at the beam waist in or proximate to crystal 103 using known spherical or cylindrical optics (not shown).

Harmonic separation block 105 can include a prism for beam separation. In one embodiment, an uncoated Pellin-Broca prism can create two beams such that one beam (i.e. the beam with the desired frequency) has minimal losses due to Fresnel reflections and the other beam (i.e. the beam with the undesired frequency) suffers significant losses due to Fresnel reflections. Notably, the output beam generated by the Pellin-Broca prism is at 90 degrees to the input beam, which allows for convenient set-up and removal of the unwanted beam (i.e. the unwanted frequency). Note that other embodiments may include generating multiple beams with desired wavelengths and/or other means for removing one or more unwanted beams having undesired frequencies. Moreover, harmonic separation block 105 may generate any number of harmonics, e.g. $2^{nd}$, $3^{rd}$, $4^{th}$ or $5^{th}$ harmonics, and/or the sum or difference frequencies of such harmonics and/or the fundamental.

Notably, beam shaping optics 106 can be positioned after crystal 103 to create a substantially circular symmetric beam profile for the output beam of laser system 100. In one embodiment, optics similar to those of beam shaping optics 102 (circular beam to elliptical beam) may be used to convert the output beam from an elliptical cross section to a circular cross section, as would be understood by those skilled in the art. However, note that in the walk-off plane (which is perpendicular to the ordinary axis and causes distortion to the beam), the divergence of the output beam is substantially similar to the divergence of the input beam, but may be a little larger due to distortion of the beam profile caused by crystal 103. In contrast, in the non-walk-off direction (i.e. at the ordinary axis), the width of the output beam will be reduced by a factor of approximately $\sqrt{2}$ because of the non-linear (approximately quadratic) conversion process. Additionally, the optics for implementing beam shaping optics 106 should also account for the shorter wavelength of the output beam. Notably, higher laser powers and/or shorter laser wavelengths allow detection of smaller defects at higher speeds. A high quality beam close to $M^2=1.0$ can be tightly focused to a small spot or narrow line, thereby facilitating the detection of small defects. Note that an $M^2$ value of 1.0 corresponds to a laser beam with an ideal Gaussian cross section. In one preferred embodiment, beam shaping optics 106 can create an output beam with an $M^2$ value that is less than about 1.2.

Although $M^2$ is one measure of beam quality, the beam quality may be further quantified by its astigmatism. In accordance with another aspect of laser system 100, beam shaping optics 102 (and beam shaping optics 106, when used) can produce a UV output laser beam with an astigmatism that causes no more than 10% of Rayleigh range shift in relative waist position for the two axes.

Note that in some applications, an elliptical output beam may better match the application for laser system 100. For example, where the UV illumination beam is incident on the wafer at an oblique angle, an elliptical laser beam would allow a circular spot. For such an application, anamorphic optics may be unnecessary for beam shaping optics 106. Alternatively, in other embodiments, the anamorphic optics of beam shaping optics 106 may change the output elliptical cross section to a different elliptical cross section than that output by beam shaping optics 102. In that embodiment, beam quality can be measured by $M_x^2$ and $M_y^2$, where x and y represent the principal axes of the ellipse (i.e. 104A and 104B in FIG. 1). In this case, both $M_x^2$ and $M_y^2$ should be less than 1.2.

In one embodiment, to reduce the defects or impurities (such as $H_2O$ and/or OH) in crystal 103, an improved annealing process can be performed. In general, annealing can be performed in an environment with less than about 20 ppm water. In one embodiment, the environment can contain clean, dry air or a dry, inert gas (such as $N_2$ or Ar).

Figure 3A:
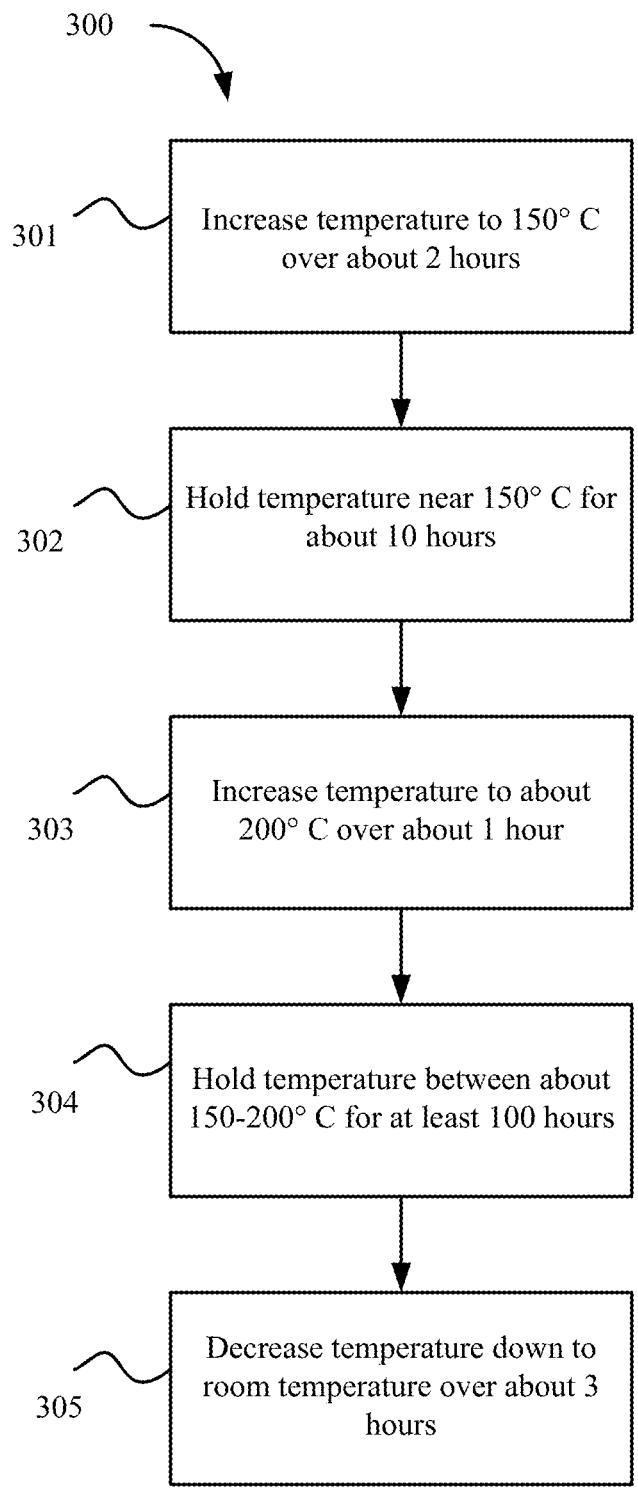
FIGS. 3A and 3B illustrate exemplary annealing processes that can be used on a frequency-conversion crystal.

In one multi-stage ramp-up annealing process 300 shown in FIG. 3A, the temperature can be slowly raised from room temperature to about 150° C. over a time interval of about 2 hours in step 301. Step 302 can hold the temperature near 150° C. for about 10-20 hours. Step 303 can then increase the temperature to about 200° C. over another approximately 1 hour period. If the initial crystal has particularly high water content, then step 303 may perform this temperature ramping slower. Then, step 304 may hold the temperature between about 150-200° C. for at least 100 hours (in some embodiments, for approximately 200 or 300 hours). On the other hand, if the initial water content is lower, then a faster temperature ramp (step 303) and a shorter anneal time (step 304) of, for example, 48 hours can be used. Step 305 can decrease the temperature down to room temperature over about 3 hours. Note that the times associated with steps 301-305 are for crystals with linear dimensions in the range of about 5-15 mm. Because the process of removing the water from the bulk of the crystal is essentially a diffusion process, crystals with larger dimensions (and hence lower surface area to volume ratios) can require longer anneal times. In contrast, crystals with smaller dimensions (and hence larger surface area to volume ratios) may be adequately annealed in a shorter time.

Moreover, the temperature ramp rate can be adjusted to ensure that no mechanical damage to the crystal occurs, whether due to water initially being driven off too fast or due to mechanical stresses induced by the temperature changes. In general, crystals with higher levels of water or with larger mechanical dimensions may need slower temperature ramps and/or longer hold times near 150° C. than smaller or drier crystals.

Figure 3B:
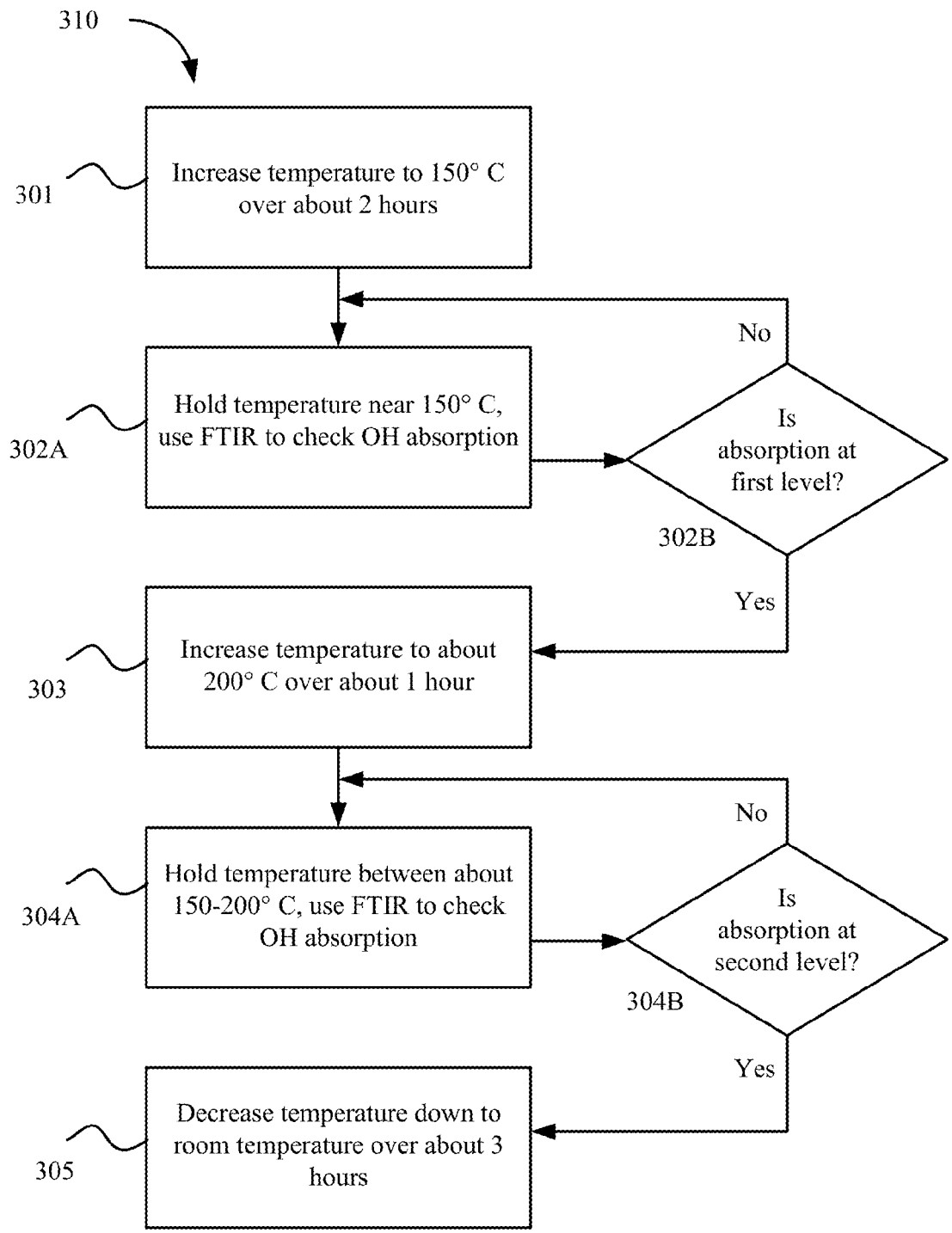

In another multi-stage ramp-up annealing process 310 shown in FIG. 3B, FTIR (Fourier transform infrared spectroscopy) may be used to monitor the absorption of —OH bonds (including $H_2O$) near 3580 cm$^{-1}$ in the infra-red spectrum. For example, FTIR monitoring can be done on a crystal while it is undergoing annealing (i.e. holding the temperature near 150° C.) in step 302A. Step 302B can determine whether the absorption is at a first level, such as the —OH absorption peak being reduced by approximately 20% from its initial value. If not, then the process continues with step 302A. If so, then the process proceeds to the annealing of step 302A. Additionally, FTIR measurement can be made on a crystal during annealing (i.e. holding the temperature between about 150-200° C.) in step 304A. Step 304B can determine whether the absorption is at a second level, such as the —OH absorption peak area has been reduced to approximately 5% of its original value. If not, then the process continues with step 304A. If so, then the process proceeds to the ramp-down of step 305.

Annealing processes 300 and 310 can be used for various frequency-conversion crystals including, for example, those made of CLBO, CBO, BBO, LBO (lithium triborate), lithium niobate, KDP, or other non-linear materials. In some embodiments, these crystals materials may contain other elements, such as dopants. Annealing processes 300 and 310 may be particularly useful for hygroscopic materials, such as CBO and CLBO. Even for some non-hygroscopic materials annealing may be useful to reduce surface or bulk contaminants.

Laser operating temperatures well below 150° C. are particularly useful when used with a high grade frequency-conversion crystal with very few defects or impurities. Notably, a crystal having minimal defects/impurities can be used at significantly lower temperatures than normal operation, thereby increasing crystal lifetime. For example, in one embodiment, crystal 103 (which was annealed using one of the above-described processes) can be used at a temperature close to, or even below, room temperature, such as an operating temperature of between about 10° C. and about 50° C. In one preferred embodiment, the operating temperature of the crystal is about 30° C. In another preferred embodiment, the crystal can be kept in a controlled environment with no water vapor and then used in very low temperatures, such as at about 0° C., −10° C. or colder. In one embodiment, a thermo-electric (or Peltier) cooler can be used to maintain and control the temperature of crystal 103.

Increasing the lifetime of the conversion crystal advantageously decreases the frequency of maintenance of the laser system and increases the percentage of the time that the inspection or metrology tool incorporating the laser system is operating productively. Increased lifetime for the crystal also means a lower operating cost for the laser system because the time interval between each service event for the laser system can be increased.

The laser system described herein can advantageously incorporate the coherence reducing schemes disclosed in U.S. patent application Ser. No. 13/073,986 (the '986 application), filed Mar. 28, 2011, now published as US20110228263, which is incorporated by reference herein. As described in the '986 application, a combination of one or more dispersive elements with one or more electro-optic modulators can be used to reduce coherence by modulating the light and by mixing spatial and temporal characteristics of the light.

Figure 4:
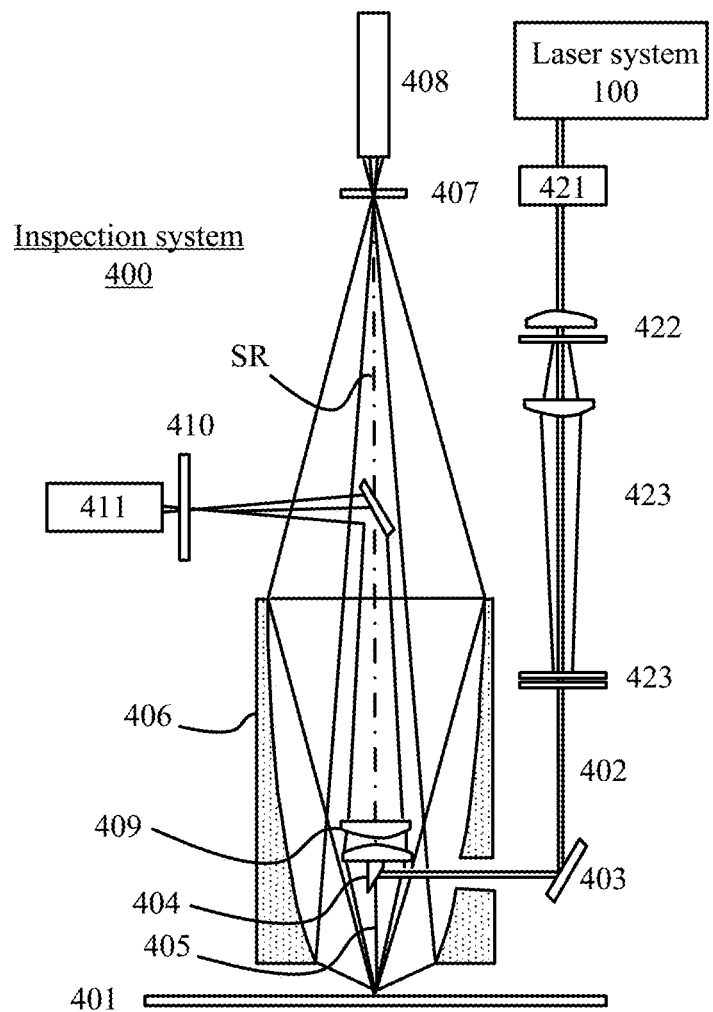
FIGS. 4, 5, 6, and 7 illustrates exemplary inspection systems including the improved laser system.

FIG. 4 illustrates a surface inspection system 400 that can be used for inspecting anomalies on a surface 401. In this embodiment, surface 401 can be illuminated by a substantially stationary illumination device portion of system 400 comprising a laser beam generated by laser system 100 (see FIG. 1). The output of laser system 100 can be consecutively passed through polarizing optics 421, a beam expander and aperture 422, and beam-forming optics 423 to expand and focus the beam.

The focused laser beam 402 is then reflected by a beam folding component 403 and a beam deflector 404 to direct the beam 405 towards surface 401 for illuminating the surface. In the preferred embodiment, beam 405 is substantially normal or perpendicular to surface 401, although in other embodiments beam 405 may be at an oblique angle to surface 401.

In one embodiment, beam 405 is substantially perpendicular or normal to surface 401 and beam deflector 404 reflects the specular reflection of the beam from surface 401 towards beam turning component 403, thereby acting as a shield to prevent the specular reflection from reaching the detectors. The direction of the specular reflection is along line SR, which is normal to surface 401. In one embodiment where beam 405 is normal to surface 401, this line SR coincides with the direction of illuminating beam 405, where this common reference line or direction is referred to herein as the axis of inspection system 400. Where beam 405 is at an oblique angle to surface 401, the direction of specular reflection SR would not coincide with the incoming direction of beam 405; in such instance, the line SR indicating the direction of the surface normal is referred to as the principal axis of the collection portion of inspection system 400.

Light scattered by small particles is collected by mirror 406 and directed towards aperture 407 and detector 408. Light scattered by large particles is collected by lenses 409 and directed towards aperture 410 and detector 411. Note that some large particles will scatter light that is also collected and directed to detector 407, and similarly some small particles will scatter light that is also collected and directed to detector 411, but such light is of relatively low intensity compared to the intensity of scattered light the respective detector is designed to detect. In one embodiment, inspection system can be configured for use in detecting defects on unpatterned wafers.

Figure 5:
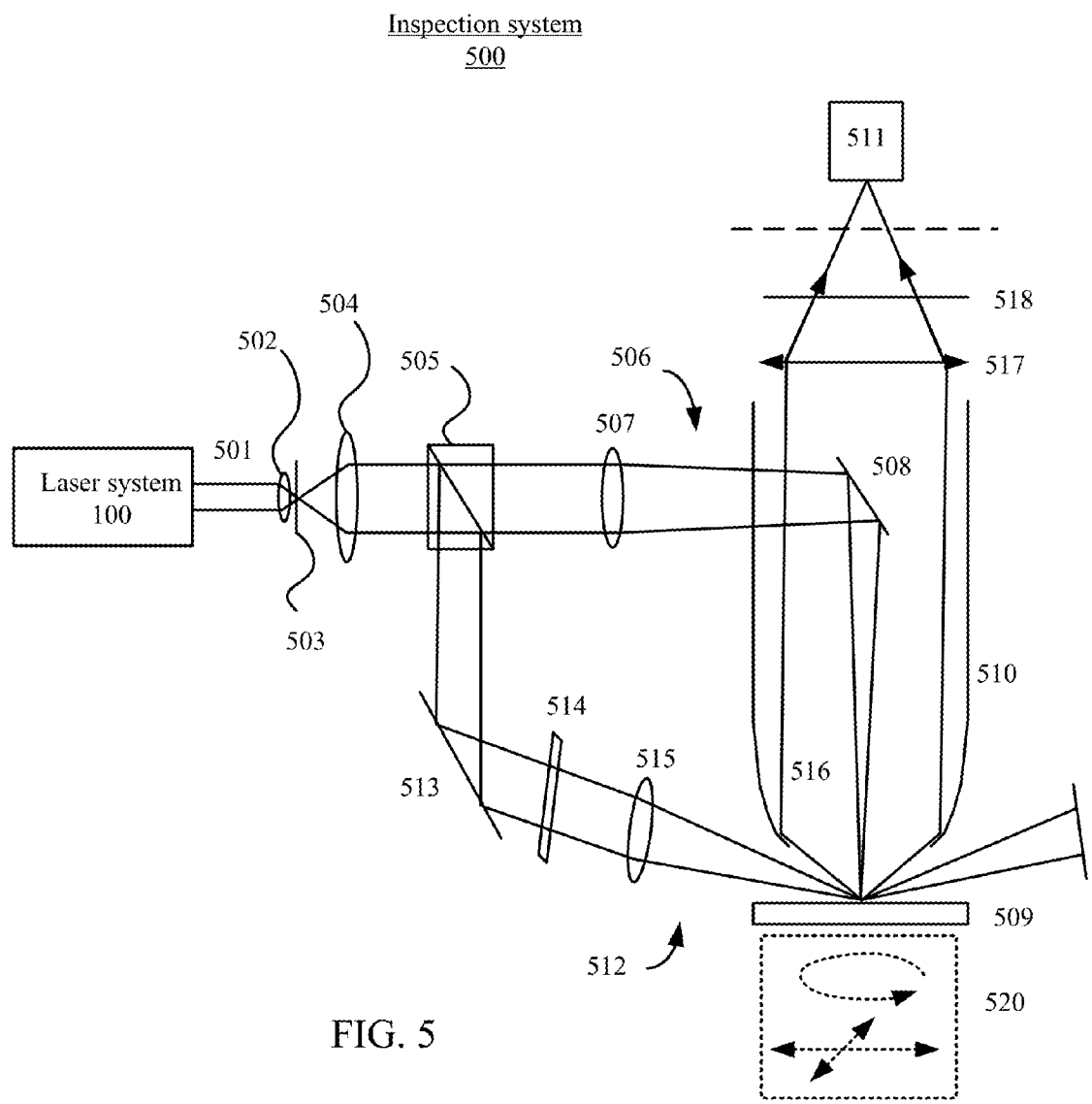

FIG. 5 illustrates an inspection system 500 configured to implement anomaly detection using both normal and oblique illumination beams. In this configuration, laser system 100 (FIG. 1) can provide a laser beam 501. A lens 502 focuses the beam 501 through a spatial filter 503 and lens 504 collimates the beam and conveys it to a polarizing beam splitter 505. Beam splitter 505 passes a first polarized component to the normal illumination channel and a second polarized component to the oblique illumination channel, where the first and second components are orthogonal. In the normal illumination channel 506, the first polarized component is focused by optics 507 and reflected by mirror 508 towards a surface of a sample 509. The radiation scattered by sample 509 is collected and focused by a paraboloidal mirror 510 to a photomultiplier tube 511.

In the oblique illumination channel 512, the second polarized component is reflected by beam splitter 505 to a mirror 513 which reflects such beam through a half-wave plate 514 and focused by optics 515 to sample 509. Radiation originating from the oblique illumination beam in the oblique channel 512 and scattered by sample 509 is collected by paraboloidal mirror 510 and focused to photomultiplier tube 511. Photomultiplier tube 511 has a pinhole entrance. The pinhole and the illuminated spot (from the normal and oblique illumination channels on surface 509) are preferably at the foci of the paraboloidal mirror 510.

The paraboloidal mirror 510 collimates the scattered radiation from sample 509 into a collimated beam 516. Collimated beam 516 is then focused by an objective 517 and through an analyzer 518 to the photomultiplier tube 511. Note that curved mirrored surfaces having shapes other than paraboloidal shapes may also be used. An instrument 520 can provide relative motion between the beams and sample 509 so that spots are scanned across the surface of sample 509.

Figure 6:
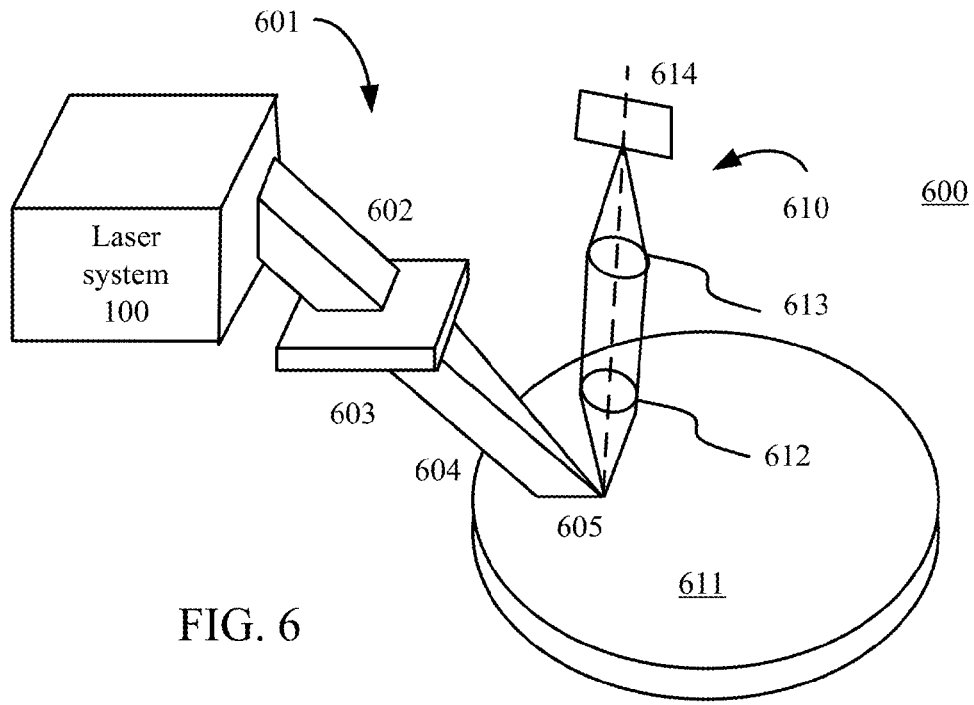

FIG. 6 illustrates another surface inspection apparatus 600 that includes illumination system 601 and collection system 610 for inspecting areas of surface 20. As shown in FIG. 6, laser system 100 (FIG. 1) is configured to direct light beam 602 through lens 603. Lens 603 is oriented so that its principal plane is substantially parallel to surface 611 and, as a result, illumination line 605 is formed on surface 611 in the focal plane of lens 603. In addition, light beam 602 and focused beam 604 are directed at a non-orthogonal angle of incidence to surface 611. In particular, light beam 602 and focused beam 604 may be directed at an angle between about 1 degree and about 85 degrees from a normal direction to surface 611. In this manner, illumination line 605 is substantially in the plane of incidence of focused beam 604.

Figure 7:
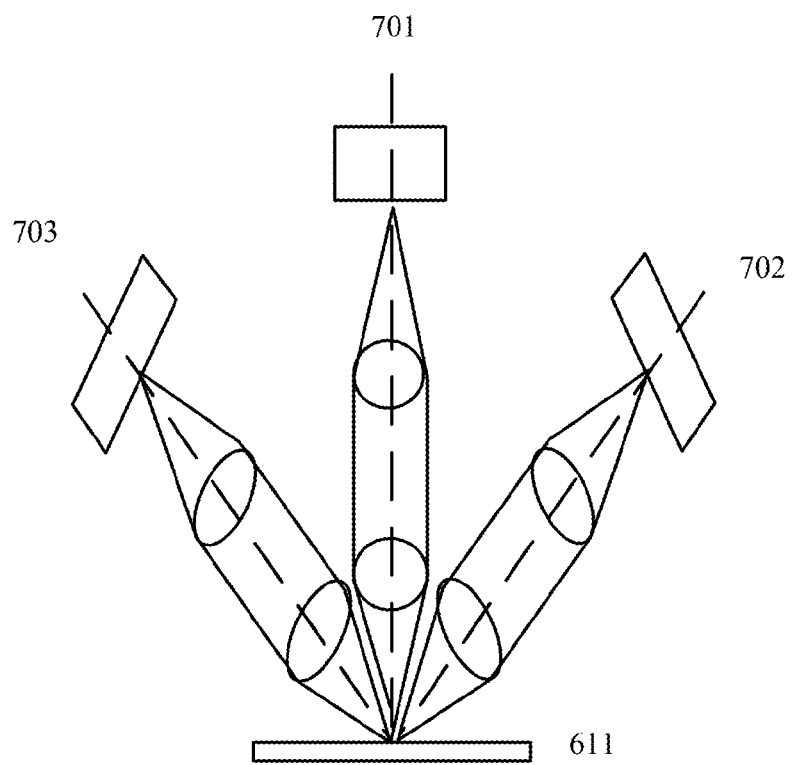

Collection system 610 includes lens 612 for collecting light scattered from illumination line 605 and lens 613 for focusing the light coming out of lens 612 onto a device, such as charge coupled device (CCD) 614, comprising an array of light sensitive detectors. In one embodiment, CCD 614 may include a linear array of detectors. In such cases, the linear array of detectors within CCD 614 can be oriented parallel to illumination line 615. In one embodiment, multiple collection systems can be included, wherein each of the collection systems includes similar components, but differ in orientation. For example, FIG. 7 illustrates an exemplary array of collection systems 701, 702, and 703 for a surface inspection apparatus (wherein its illumination system, e.g. similar to that of illumination system 601, is not shown for simplicity).

U.S. Pat. Nos. 5,108,176, 5,377,001, 5,377,002, 5,189,481, 5,712,701, 6,118,525, 6,201,601, 6,271,916, 6,608,676, 7,088,443, 7,492,451, 7,525,649, and 7,957,066 as well as U.S. Published Applications 2009/0180176, and 2011/0073982 (all incorporated by reference herein) describe other inspection systems embodiments that can include laser system 100. Laser system 100 can also be combined with one or more of the pulse stretching and pulse rate multiplication schemes disclosed in U.S. Provisional Patent Application 61/496,446, filed Jun. 13, 2011, which is incorporated by reference herein.

Figure 8:
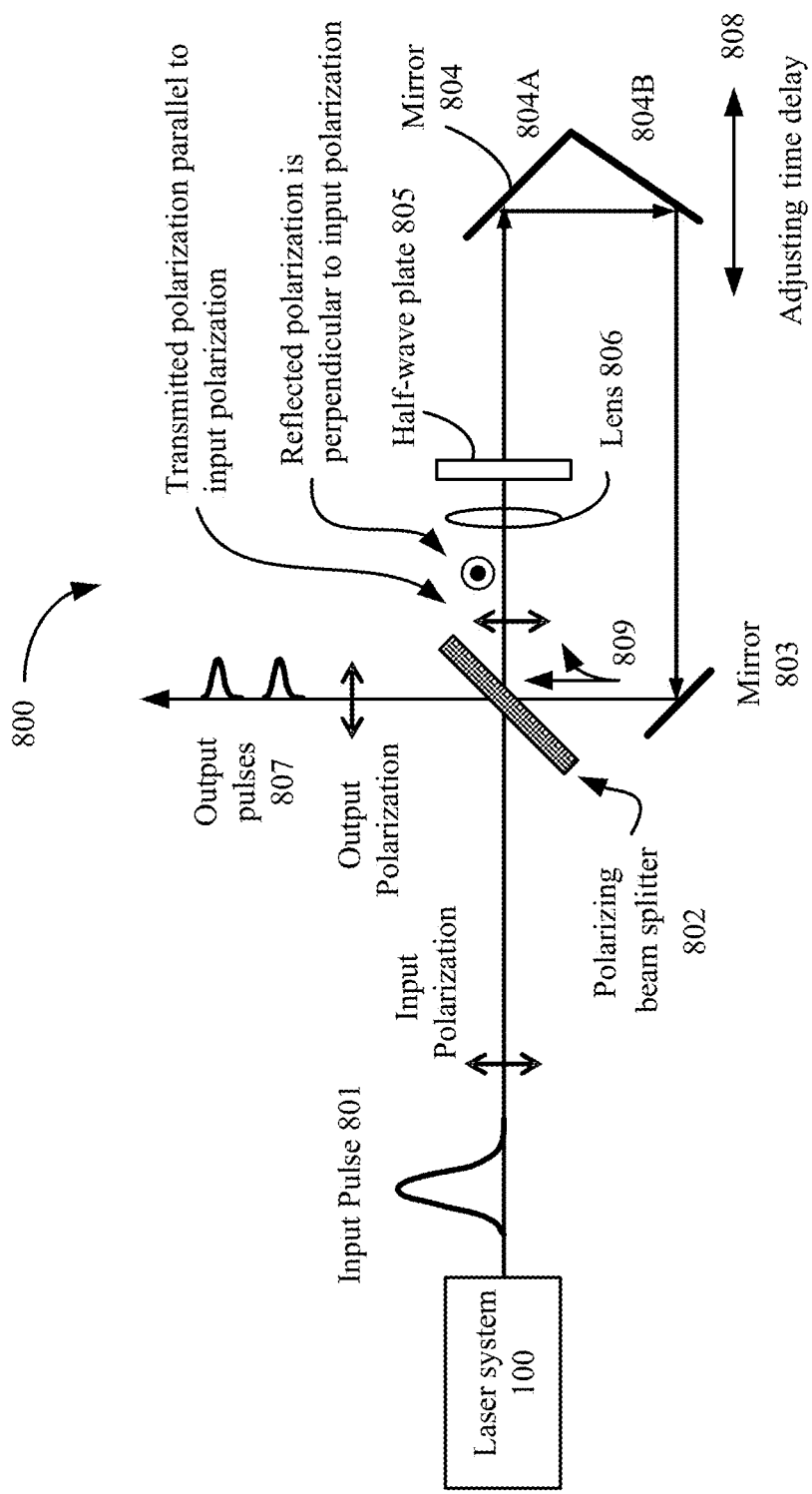
FIG. 8 illustrates an exemplary pulse multiplier configured to generate pulse trains from each input laser pulse generated by the improved laser system.

FIG. 8 illustrates an exemplary pulse multiplier 800 configured to generate pulse trains from each input pulse 801 output by laser system 100 (FIG. 1). Input pulse 801 impinges on a polarizing beam splitter 802, which because of the input polarization of input pulse 801, transmits all of its light to a lens 806. Thus, the transmitted polarization is parallel to the input polarization of input pulse 801. Lens 806 focuses and directs the light of input pulse 801 to a half-wave plate 805. In general, a wave plate can shift the phases between perpendicular polarization components of a light wave and hence change the polarization state of the light passing through it. In a wave plate, one polarization component propagates slightly slower than the perpendicular component. Half-wave plate 805 is fabricated such that for light exiting, one polarization component is substantially half of a wavelength delayed (180 degrees) relative to the other polarization component. In some preferred embodiments, half-wave plate 805 is oriented such that its optical axis is at substantially 27.4° to the plane of the input polarization. Thus, when light with the input polarization strikes the half-wave plate 805, its polarization is rotated by substantially 54.8° in these preferred embodiments.

The light exiting half-wave plate 805 is reflected by mirrors 804 and 803 back to polarizing beam splitter 802. Thus, polarizing beam splitter 802, lens 806, half-wave plate 805, and mirrors 804 and 803 form a ring cavity configuration. The light impinging on polarizing beam splitter 802 after traversing the ring cavity is polarized at angle relative to the input polarization (an angle of substantially 54.8° in some preferred embodiments) because of half-wave plate 805. Therefore, polarizing beam splitter 802 transmits some light and reflects other light, as indicated by arrows 809. Specifically, polarizing beam splitter 802 transmits the light from mirror 803 having the same polarization as input pulse 801. This transmitted light exits pulse multiplier 800 as output pulses 807. The reflected light, which has a polarization perpendicular to that of input pulse 801, is re-introduced into the ring cavity (pulses not shown for simplicity). In those preferred embodiments with the half-wave plate 805 axis oriented at substantially 27.4° to the input polarization, substantially two thirds of the energy of a single incident pulse will be reflected back into the ring cavity and substantially one third of the incident energy single pulse will be transmitted.

Notably, these re-introduced pulses can traverse the ring in the manner described above with further polarization rotation by half-wave plate 805 and then light splitting by polarizing beam splitter 802. Thus, in general, the above-described ring cavity is configured to allow some light to exit and the rest of the light (with some minimal losses) to continue around the ring. During each traversal of the ring if no additional input pulses were introduced, the energy of the total light would decrease due to the light exiting the ring as output pulses 807.

Periodically, a new input pulse 801 is provided to pulse multiplier 800. The size of the ring, and thus the time delay of the ring, can be adjusted by moving mirror 804 along the axis indicated by arrows 808. If the time delay of the ring is adjusted to be approximately half the repetition time between pulses from the laser 100, then half the output pulses will be approximately halfway between input pulses and the other half of the pulses from the ring will approximately coincide with input pulses.

In one exemplary embodiment, the laser might have a repetition rate of 125 MHz and a pulse width of approximately 10 to 20 ps, and the cavity could have a delay time of 4.05 ns, so that a pulse that has made one trip around the cavity arrives approximately half way between two input pulses and a second pulse that has made two round trips arrives approximately 100 ps after the next input laser pulse. So a steady stream of narrow input pulses at 125 MHz in this example embodiment would be turned into a stream of much broader pulses at a repetition rate of 250 MHz (broadened because the cavity time has deliberately been set to be close to, but not exactly, half the time interval between input pulses). In the preferred embodiment where the optical axis of the half-wave plate is oriented at substantially 27.4° to the polarization of the input pulse, the output pulses will be substantially equal to one another in total energy.

The various embodiments of the structures and methods of this invention that are described above are illustrative only of the principles of this invention and are not intended to limit the scope of the invention to the particular embodiments described. For example, the above-described inspection systems can be incorporated into either dark-field inspection tools or bright-field inspection tools. Thus, the invention is limited only by the following claims and their equivalents.

The invention claimed is:

1. A method of annealing a frequency-conversion crystal, the method comprising:
   increasing a temperature to about 150° C. over about 2 hours;
   holding the temperature near 150° C. for about 10 hours;
   increasing the temperature to about 200° C. over about 1 hour;
   holding the temperature between 150-200° C. for about 100 hours or longer; and
   decreasing the temperature down to close to room temperature over about 3 hours.

2. A method of annealing a frequency-conversion crystal, the method comprising:
   (a) increasing a temperature to about 150° C. over about 2 hours;
   (b) holding the temperature near 150° C. for about 10 hours;
   (c) during step (b), determining whether —OH bonds absorption is at a first level, wherein if not, then continuing to hold the temperature near 150° C., and if so, then proceeding to (d);
   (d) increasing the temperature to about 200° C. over about 1 hour;
   (e) holding temperature between 150-200° C. for about 100 hours;
   (f) during step (e), determining whether the —OH bonds absorption is at a second level, wherein if not, then continuing to hold the temperature between 150-200° C., and if so, then proceeding to (g); and
   (g) decreasing the temperature down to substantially room temperature over about 3 hours.

3. The method of claim 2, wherein the determining uses FTIR (Fourier transform infrared spectroscopy).

4. The method of claim 3, wherein the FTIR monitors the —OH bonds near 3580 cm$^{-1}$ in an infra-red spectrum.

5. A multi-stage ramp-up annealing process for reducing an amount of a contaminant in a crystal comprising:
   a first ramp-up stage of increasing a temperature of the crystal to a first predetermined temperature;
   holding the crystal at the first predetermined temperature such that the amount of said contaminant in the crystal is reduced from an original amount to a first level;
   a second ramp-up stage of increasing the temperature of the crystal to a second predetermined temperature, the second predetermined temperature being higher than the first predetermined temperature;
   holding the crystal at the second predetermined temperature such that the amount of said contaminant in the crystal is reduced from the first level to a second level; and
   decreasing the temperature of the crystal to close to room temperature.

6. The method of claim 5, wherein said method comprises reducing an amount of water in said crystal.

7. The method of claim 6, further comprising disposing the crystal in an environment having less than 20 ppm water during the first ramp-up stage, during said holding, during said second ramp-up stage and during said decreasing said temperature.

8. The method of claim 7,
   wherein said first ramp-up state comprises gradually increasing the temperature of said environment to about 150° C.;
   wherein holding the crystal at the first predetermined temperature comprises maintaining the environment at 150° C.;
   wherein said second ramp-up state comprises gradually increasing the temperature of said environment from 150° C. to about 200° C.;
   wherein holding the crystal at the second predetermined temperature comprises maintaining the environment at about 200° C.; and
   wherein decreasing the temperature comprises gradually reducing the environment from about 200° C. to room temperature.

9. The method of claim 8,
   wherein increasing the temperature of said environment to about 150° C. comprises gradually increasing a temperature of the crystal over about 2 hours;
   wherein maintaining the environment at 150° C. comprises holding the crystal at 150° C. for about 10 hours;

wherein increasing the temperature of said environment from 150° C. to about 200° C. comprises gradually increasing the temperature of the crystal over about about 1 hour;

wherein maintaining the environment at about 200° C. comprises holding the crystal at 200° C. for about 100 hours; and wherein reducing the environment to room temperature comprises gradually decreasing the temperature of the crystal to room temperature over about 3 hours.

10. The method of claim 8, wherein holding the crystal at the first predetermined temperature further comprises determining whether —OH bonds absorption is at a first level, wherein if not, then continuing to hold the temperature near 150° C., and if so, then performing said increasing the temperature of said environment from 150° C. to about 200° C., and wherein holding the crystal at the second predetermined temperature further comprises determining whether the —OH bonds absorption is at a second level, wherein if not, then continuing to hold the temperature between 150-200° C., and if so, then performing said reducing the environment to room temperature.

11. The method of claim 10, wherein said determining comprises utilizing FTIR (Fourier transform infrared spectroscopy).

12. A multi-stage ramp-up annealing process for reducing an amount of water in a hygroscopic material comprising:

a first ramp-up stage of increasing a temperature of the hygroscopic material disposed in an environment having less than 20 ppm water to a first predetermined temperature;

holding the hygroscopic material at the first predetermined temperature in said environment until —OH bonds absorption is at a first level;

a second ramp-up stage of increasing the temperature of the hygroscopic material in said environment to a second predetermined temperature, the second predetermined temperature being higher than the first predetermined temperature;

holding the hygroscopic material in said environment at the second predetermined temperature until the —OH bonds absorption is at a second level; and decreasing the temperature of the hygroscopic material to close to room temperature.

13. A method of annealing a frequency-conversion crystal, the method comprising:

changing a temperature of the frequency-conversion crystal to a first set point;

holding the temperature of the frequency-conversion crystal at the first set point for a pre-bake period;

changing the temperature of the frequency-conversion crystal to a second set point;

holding the temperature of the frequency-conversion crystal at the second set point for the baking period;

changing the temperature of the frequency-conversion crystal to substantially room temperature.

14. The annealing method of claim 13, wherein the first set point is greater than 100° C.

15. The annealing method of claim 13, wherein the pre-bake period is greater than 4 hours.

16. The annealing method of claim 13, wherein the second set point is greater than 150° C.

17. The annealing method of claim 13, wherein the baking period is greater than 50 hours.

18. The annealing method of claim 13, wherein the frequency-conversion crystal is measured during the baking process to determine if the annealing is complete.

19. The method of claim 18, wherein the determining uses FTIR (Fourier transform infrared spectroscopy).

20. The method of claim 19, wherein the FTIR monitors the —OH bonds near 3580 cm$^{-1}$ in an infra-red spectrum.

* * * * *